US012201441B2

(12) United States Patent
Woolf et al.

(10) Patent No.: US 12,201,441 B2
(45) Date of Patent: Jan. 21, 2025

(54) BIOMARKERS OF NEUROPATHIC PAIN

(71) Applicants: Children's Medical Center Corporation, Boston, MA (US); Beth Israel Deaconess Medical Center, Inc., Boston, MA (US)

(72) Inventors: Clifford J. Woolf, Newton, MA (US); Alban A. Latremoliere, Baltimore, MD (US); Thomas E. Scammell, Wellesley, MA (US); Chloe M. Alexandre, Baltimore, MD (US)

(73) Assignees: Children's Medical Center Corporation, Boston, MA (US); Beth Israel Deaconess Medical Center, Inc., Boston, MA (US)

( * ) Notice: Subject to any disclaimer, the term of this patent is extended or adjusted under 35 U.S.C. 154(b) by 1073 days.

(21) Appl. No.: 17/251,755

(22) PCT Filed: Jun. 13, 2019

(86) PCT No.: PCT/US2019/037063
§ 371 (c)(1),
(2) Date: Dec. 11, 2020

(87) PCT Pub. No.: WO2019/241564
PCT Pub. Date: Dec. 19, 2019

(65) Prior Publication Data
US 2021/0386365 A1    Dec. 16, 2021

Related U.S. Application Data
(60) Provisional application No. 62/684,599, filed on Jun. 13, 2018.

(51) Int. Cl.
| | |
|---|---|
| A61B 5/00 | (2006.01) |
| A61B 5/374 | (2021.01) |
| A61B 5/397 | (2021.01) |
| A61K 31/195 | (2006.01) |
| A61K 31/55 | (2006.01) |
| A61P 29/00 | (2006.01) |

(52) U.S. Cl.
CPC ............ *A61B 5/4809* (2013.01); *A61B 5/374* (2021.01); *A61B 5/397* (2021.01); *A61B 5/4812* (2013.01); *A61B 5/4824* (2013.01); *A61K 31/195* (2013.01); *A61K 31/55* (2013.01); *A61P 29/00* (2018.01)

(58) Field of Classification Search
None
See application file for complete search history.

(56) References Cited

U.S. PATENT DOCUMENTS

| | | |
|---|---|---|
| 6,768,920 B2 | 7/2004 | Lange et al. |
| 8,920,382 B1 | 12/2014 | Hauswald |

(Continued)

OTHER PUBLICATIONS

Alexandre et al., "Decreased alertness due to sleep loss increases pain sensitivity in mice," Nature Medicine, Jun. 2017, 23(6):768, 18 pages.

(Continued)

*Primary Examiner* — Sana Sahand
(74) *Attorney, Agent, or Firm* — Fish & Richardson P.C.

(57) ABSTRACT

This disclosure is related to methods of objectively detecting and measuring neuropathic pain in a subject.

13 Claims, 22 Drawing Sheets

(56) References Cited

U.S. PATENT DOCUMENTS

| | | |
|---|---|---|
| 2003/0204148 A1 | 10/2003 | Lange et al. |
| 2004/0077967 A1 | 4/2004 | Jordan |
| 2007/0092858 A1 | 4/2007 | Usmani et al. |
| 2009/0076407 A1 | 3/2009 | John et al. |
| 2010/0063349 A1 | 3/2010 | He et al. |
| 2013/0245605 A1 | 9/2013 | Candiotti |
| 2013/0310660 A1* | 11/2013 | Zuckerman-Stark ........................ A61B 5/392 600/301 |
| 2017/0145015 A1* | 5/2017 | Pardal Filipe ....... A61K 9/2095 |
| 2018/0192942 A1* | 7/2018 | Clark ................... A61B 5/1128 |
| 2018/0229040 A1* | 8/2018 | Srivastava ......... A61N 1/36071 |

OTHER PUBLICATIONS

Al-Saad et al., "EMG and Pain Severity Evaluation in Patients with TMD Using Two Different Occlusal Devices," International Journal of Prosthodontics, Jan. 1, 2001, 14(1), 15-21.

Czarnik et al., "Encoding methods for combinatorial chemistry," Current Opinion in Chemical Biology, Jun. 1, 1997, 1(1):60-6.

Endo et al., "Selective and total sleep deprivation: effect on the sleep EEG in the rat," Psychiatry Research, Feb. 7, 1997, 66(2-3):97-110.

Franken et al., "Sleep deprivation in rats; effects on EEG power spectra, vigilance states, and cortical temperature," American Journal of Physiology-Regulatory, Integrative and Comparative Physiology, Jul. 1, 1991, 261(1):R198-208.

Gore et al., "Pain severity in diabetic peripheral neuropathy is associated with patient functioning, symptom levels of anxiety and depression, and sleep," Journal of Pain and Symptom Management, Oct. 1, 2005, 30(4):374-85.

Institutional Animal Care and Use Committee, "Other Species: Analgesia and Anesthesia Formulary," The University of North Carolina at Chapel Hill, 2015, pp. 4 and 15, Total Intra-venous Anesthesia, TIVA section, 32 pages.

Kontinen et al., "Sleep and EEG patterns in the chronic constriction injury model of neuropathic pain," Physiology & Behavior, Feb. 1, 2003, 78(2):241-6.

Moldofsky, "Sleep and pain," Sleep Medicine Reviews, Oct. 1, 2001, 5(5):385-96.

Nir et al., "Pain assessment by continuous EEG: association between subjective perception of tonic pain and peak frequency of alpha oscillations during stimulation and at rest," Brain Research, Jul. 16, 2010, 1344:77-86.

PCT International Preliminary Report on Patentability in International Appln. No. PCT/US2019/03706, dated Oct. 15, 2020, 14 pages.

PCT International Search Report and Written Opinion in International Appln. No PCT/US2019/037063, dated Aug. 29, 2019, 16 pages.

Rochrs et al., "Sleep and pain; interaction of two vital functions," Seminars in Neurology, Mar. 2005, 25(1):106-16.

Scammell et al., "International Working Group on Rodent Models of Narcolepsy: A consensus definition of cataplexy in mouse models of narcolepsy," Sleep, Jan. 1, 2009, 32(1):111-6.

Scammell et al., "Neural circuitry of wakefulness and sleep," Neuron, Feb. 22, 2017, 93(4):747-65.

Serlin et al., "When is cancer pain mild, moderate or severe? Grading pain severity by its interference with function," Pain, May 1, 1995, 61(2):277-84.

Svetnik et al., "Insight into reduction of wakefulness by suvorexant in patients with insomnia: analysis of wake bouts," Sleep, Jan. 2018, 41(1):zsx178.

Tobler et al., "Sleep and sleep regulation in normal and prion protein-deficient mice," Journal of Neuroscience, Mar. 1, 1997, 17(5):1869-79.

Wolpert, "A Manual of Standardized Terminology, Techniques and Scoring System for Sleep Stages of Human Subjects," Archives of General Psychiatry, Feb. 1, 1969, 20(2):246-7.

Woolf, "What is this thing called pain?," The Journal of Clinical Investigation, Nov. 1, 2010, 120(11):3742-4.

* cited by examiner

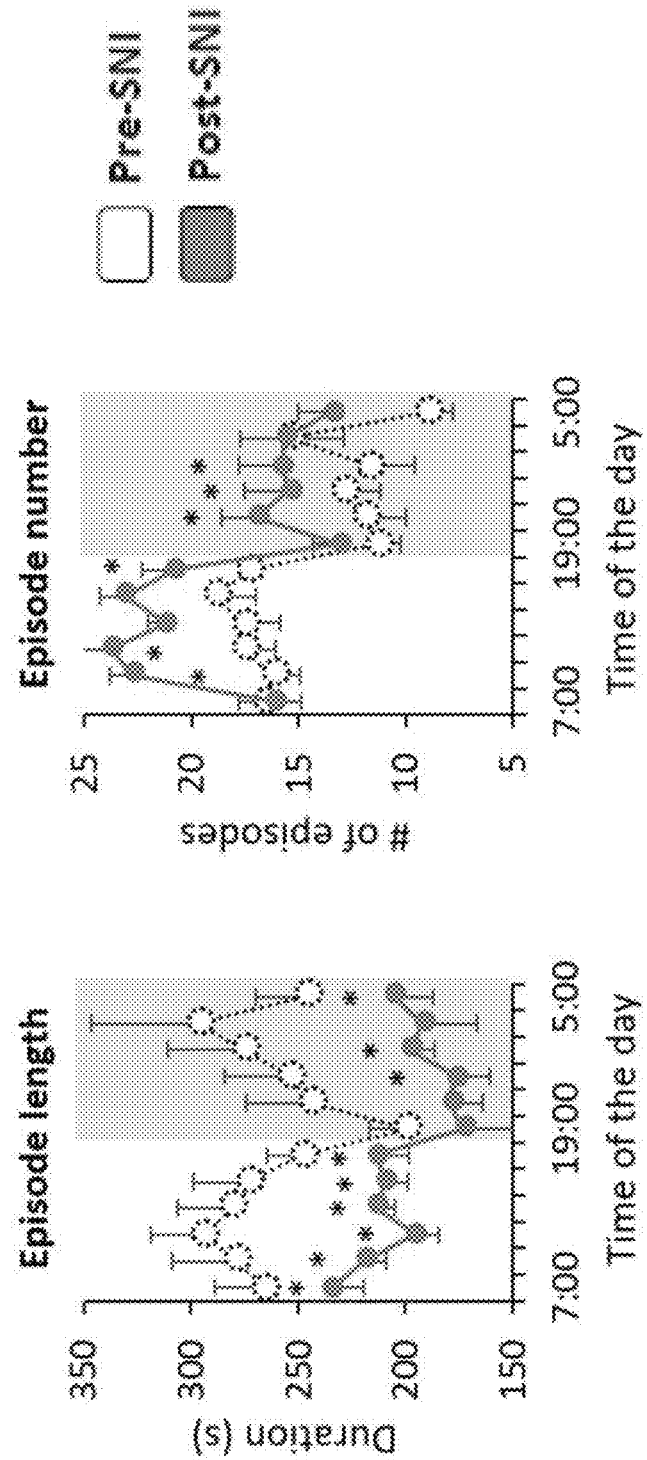

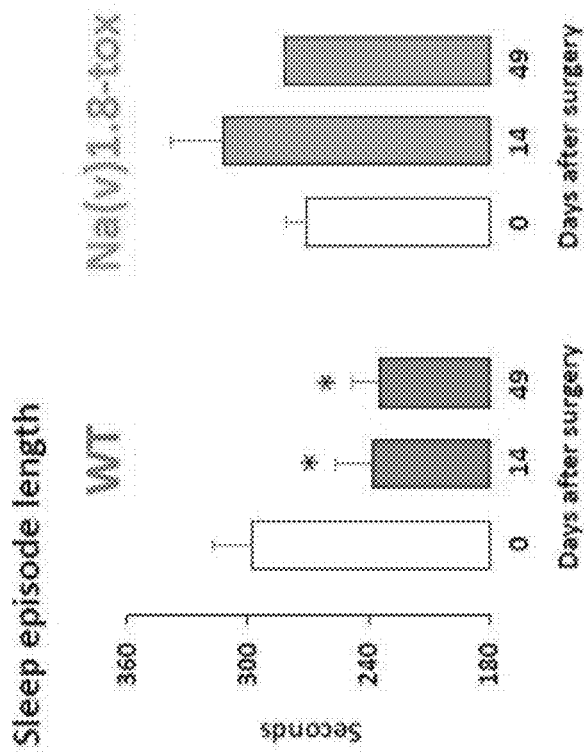
FIG. 7B
FIG. 7C
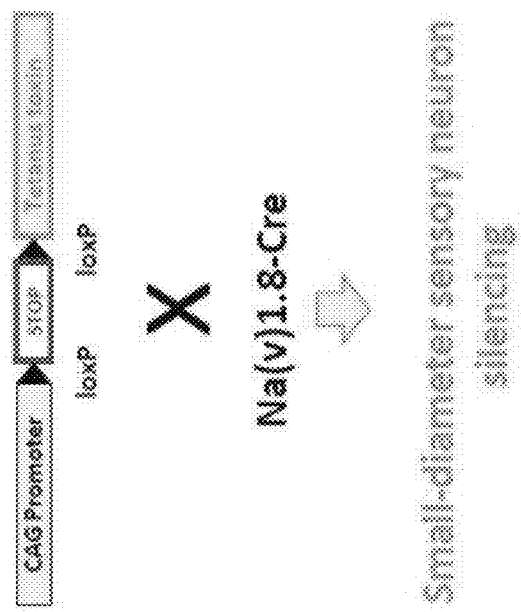
FIG. 7A

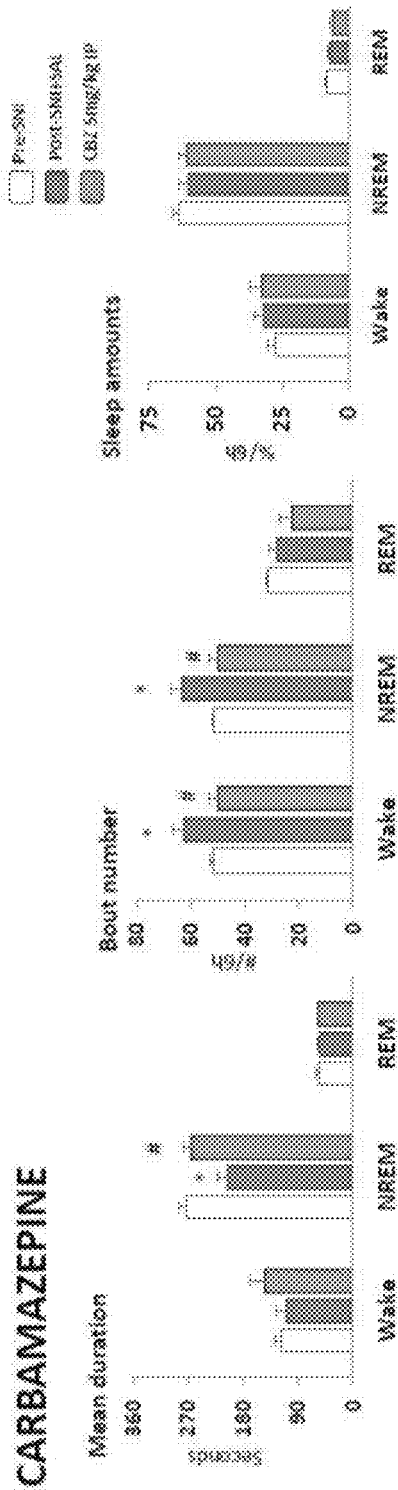

BIOMARKERS OF NEUROPATHIC PAIN

CLAIM OF PRIORITY

This application is a national phase application of PCT/US2019/037063, filed Jun. 13, 2019, which claims the benefit of U.S. Provisional Application Ser. No. 62/684,599, filed on Jun. 13, 2018. The entire contents of the foregoing are incorporated herein by reference.

STATEMENT OF FEDERALLY SPONSORED RESEARCH

This invention was made with government support under Grant No. R01 DE022912 awarded by the National Institutes of Health. The Government has certain rights in the invention.

TECHNICAL FIELD

This disclosure is related to methods of objectively detecting and measuring neuropathic pain in a subject.

BACKGROUND

Pain is a distressing feeling often caused by intense or damaging stimuli or by alterations in the function of the nervous system. It is an unpleasant sensory and emotional experience often associated with actual or potential tissue damage, or described in terms of such damage. Because pain is a subjective phenomenon, it has frequently defied objective, quantitative measurement. Traditionally, physicians have had to assess a patient's pain by relying on the patient's own description of the pain. However, self-description is often inaccurate and difficult to compare to the description of another subject.

Thus, there is a need to objectively measure the pain, particularly neuropathic pain, in a subject for diagnostic purposes and for clinical trials, and assess effectiveness of therapeutic interventions for treating pain (e.g., neuropathic pain).

SUMMARY

This disclosure is related to methods of objectively measuring episodes of spontaneous neuropathic pain in a subject using various biomarkers, including e.g., frequency of brief awakenings (BAs), number of BAs in a predetermined period of time, average duration of non-rapid eye movement sleep (NREMS) episodes, and the total number of non-rapid eye movement sleep (NREMS) episodes (during a specific period of time), among others. These methods are based, at least in part, on the finding in mouse models of peripheral neuropathic pain that nerve injury does not cause changes in total amount of wake and sleep time and does not affect the general circadian sleep-wake pattern, but causes severe fragmentation of NREMS by very brief episodes of awakenings. The degree of fragmentation is much higher than the degree of fragmentation in normal subjects or in subjects stimulated with innocuous (touch) stimuli. The present disclosure provides an objective way to measure episodes of neuropathic pain (e.g., spontaneous neuropathic pain).

In one aspect, the disclosure is related to methods of determining that a subject is experiencing neuropathic pain. The methods involve detecting an increase in frequency of brief awakenings (BAs) during sleep of the subject as compared to a reference level; thereby determining that the subject is experiencing neuropathic pain. In some embodiments, the neuropathic pain is spontaneous neuropathic pain.

In some embodiments, the methods further involve administering to the subject an analgesic agent prior to, during, and/or after detecting an increase in frequency of BAs during sleep of the subject.

In some embodiments, the BAs disrupt non-rapid eye movement sleep (NREMS) of the subject.

In some embodiments, the reference level is the average frequency of BAs in subjects who do not have neuropathic pain.

In some embodiments, the frequency of BAs of the subject is at least 20%, 30%, 40%, or 50% more than the reference level. In some embodiments, the frequency of BAs is measured by the number of BAs during sleep.

In some embodiments, each BA lasts from about 2 seconds to about 30 seconds.

In some embodiments, the BAs are detected by electroencephalogram (EEG) and electromyogram (EMG). In some embodiments, the BAs are characterized by a high-frequency low amplitude EEG signal and an increase of EMG tone.

In some embodiments, the analgesic agent is a narcotic analgesic, an anticonvulsant agent, a corticosteroid, a secondary amine tricyclic antidepressant (TCA), a selective serotonin norephinephrine reuptake inhibitor, a calcium channel a2-d ligand, a N-methyl-D-aspartate (NMDA) receptor antagonist, or a sepiapterin reductase inhibitor, or any combination thereof.

In some embodiments, the analgesic agent is alfentanil, almotriptan, buprenorphine, butalbital, butorphanol, codeine, diflunisal, dihydrocodeine, diphenhydramine, eletriptan, ergotamine, fentanyl, frovatriptan, gabapentanoid, hydrocodone, hydromorphone, isometheptene mucate, levorphanol, mefenamic acid, meperidine, methadone, morphine, nalbuphine, naratriptan, oxycodone, oxymorphone, phenyltoloxamine, piroxicam, propoxyphene, rizatriptan, sumatriptan, tapentadol, tolmetin, tramadol, ziconotide, or zolmitriptan, or any combination thereof.

In some embodiments, the analgesic agent is nortriptyline, desipramine, duloxetine, venlafaxine, gabapentin, pregabalin, lidocaine, Carbamazepine, Lacosamide, Lamotrigine, Oxcarbazepine, Topiramate, Valproate, sulfasalazine, capsaicin, Mexiletine, dextromethorphan, memantine, Tetrahydrocannabinol, or botulin toxin, or any combination thereof.

In some embodiments, the subject is a human subject.

In another aspect, the disclosure also provides methods of determining that a subject is experiencing neuropathic pain. The methods involve detecting an increase in the number of brief awakenings (BAs) during sleep of the subject in a predetermined period as compared to a reference level, thereby determining that the subject is experiencing neuropathic pain.

In some embodiments, the neuropathic pain is spontaneous neuropathic pain.

In some embodiments, the methods also involve administering to the subject an analgesic agent.

In some embodiments, the reference level is the average number of BAs during the predetermined period in subjects who do not have neuropathic pain.

In some embodiments, the number of BAs during the predetermined period of the subject is at least 20%, 30%, 40%, or 50% more than the reference level.

In some embodiments, the length of the predetermined period is 12 hours.

In one aspect, the disclosure is also related to methods of adjusting treatment administered to a subject having neuropathic pain. The methods involve (a) administering a first analgesic agent to a subject; (b) determining a frequency of brief awakenings (BAs) during sleep; and (c) continuing treating the subject with the analgesic agent if the subject has a decrease in frequency of BAs as compared to a reference level; or administering to the subject a second analgesic agent if the subject has an increase in frequency of BAs or does not have a decrease in frequency of BAs as compared to the reference level.

In some embodiments, the neuropathic pain is spontaneous neuropathic pain.

In some embodiments, the reference level is a frequency of BAs of the subject during sleep before being administered with the first analgesic agent. In some embodiments, the reference level is the average frequency of BAs in subjects who do not have neuropathic pain.

In one aspect, the disclosure is also related to methods of adjusting treatment for a subject having neuropathic pain. The methods involve (a) administering a first analgesic agent to a subject; (b) determining the number of brief awakenings (BAs) during sleep of the subject in a predetermined period; and (c) continuing treating the subject with the analgesic agent if the subject has a decrease in the number of BAs as compared to a reference level; or administering to the subject a second analgesic agent if the subject has an increase in the number of BAs or does not have a decrease in the number of BAs as compared to the reference level.

In some embodiments, the neuropathic pain is spontaneous neuropathic pain.

In some embodiments, the reference level is the number of BAs of the subject during sleep before being administered with the first analgesic agent. In some embodiments, the reference level is the average number of BAs in subjects who do not have neuropathic pain.

In one aspect, the disclosure also provides methods of adjusting treatment for a subject having neuropathic pain. The methods involve determining a frequency of brief awakenings (BAs) of the subject during sleep, wherein the subject is being treated with an analgesic agent; determining that the frequency of BAs is different from a reference level; and adjusting treatment for the subject having neuropathic pain.

In some embodiments, the neuropathic pain is spontaneous neuropathic pain.

In some embodiments, adjusting treatment comprises increasing dosage of the analgesic agent if the frequency of BAs is higher than the reference level. In some embodiments, adjusting treatment comprises decreasing dosage of the analgesic agent if the frequency of BAs is lower than the reference level.

In some embodiments, the reference level is the frequency of BAs of the subject during sleep prior to being treated with the analgesic agent. In some embodiments, the reference level is the average frequency of BAs in subjects who do not have neuropathic pain.

In one aspect, the disclosure also provides methods of adjusting treatment for a subject having pain. The methods involve determining a number of brief awakenings (BAs) of the subject during sleep in a predetermined period, wherein the subject is being treated with an analgesic agent; comparing the number of BAs to a reference level; and adjusting treatment for the subject having pain.

In some embodiments, the neuropathic pain is spontaneous neuropathic pain.

In some embodiments, adjusting treatment comprises increasing dosage of the analgesic agent if the number of BAs is higher than the reference level. In some embodiments, adjusting treatment comprises decreasing dosage of the analgesic agent if the number of BAs is lower than the reference level.

In one aspect, the disclosure is related to methods of identifying an analgesic agent for treating neuropathic pain. The methods involve administering a test agent to a subject with neuropathic pain; determining that the subject has a decrease in frequency of brief awakenings (BAs) during sleep as compared to a reference level; and identifying the test agent as an analgesic agent for treating neuropathic pain.

In some embodiments, the neuropathic pain is spontaneous neuropathic pain.

In some embodiments, the reference level is the frequency of BAs in the subject prior to being treated by the test agent.

In some embodiments, the subject is a human. In some embodiments, the subject is a mammalian model of neuropathic pain (e.g., a mouse, a rat, a rabbit, a guinea pig, or a monkey).

In one aspect, the disclosure is also related to methods of identifying an analgesic agent for treating neuropathic pain. The methods involve administering a test agent to a subject with neuropathic pain; determining that the subject has a decrease in the number of brief awakenings (BAs) during sleep in a predetermined period as compared to a reference level; and identifying the test agent as an analgesic agent for treating neuropathic pain.

In some embodiments, the neuropathic pain is spontaneous neuropathic pain.

In some embodiments, the reference level is the number of BAs in the subject during sleep in the predetermined period prior to being treated by the test agent.

In another aspect, the disclosure provides methods of measuring neuropathic pain in a subject. The methods involve detecting frequency of brief awakenings (BAs) of the subject during sleep, wherein the frequency of BAs indicates severity of neuropathic pain.

In one aspect, the disclosure provides method of measuring neuropathic pain in a subject. The methods involve determining the number of brief awakenings (BAs) during sleep in a predetermined period, wherein the number of BAs indicates severity of neuropathic pain.

In one aspect, the disclosure provides methods of measuring neuropathic pain in a subject. The methods involve determining average duration of non-rapid eye movement sleep (NREMS) episodes of the subject, wherein the average duration of NREMS is negatively correlated with severity of neuropathic pain.

In one aspect, the disclosure provides methods of measuring neuropathic pain in a subject. The methods involve determining the number of non-rapid eye movement sleep (NREMS) episodes of the subject in a predetermined period, wherein the number of NREMS episodes indicates severity of neuropathic pain.

In some embodiments, the neuropathic pain is spontaneous neuropathic pain.

As used herein, the term "brief awakening" or "BA" refers to abrupt changes in EEG frequencies (indicating an awake state) and brief increases in EMG amplitude that last typically less than 30 seconds. The brief awakenings disrupt sleep continuity and cause sleep fragmentation.

As used herein, the term "neuropathic pain" refers to pain caused by damage or disease affecting the somatosensory nervous system (e.g., peripheral and central nervous system).

As used herein, the terms "subject" and "patient" are used interchangeably throughout the specification and describe an animal, human or non-human, to whom treatment according to the methods of the present disclosure is provided. Veterinary and non-veterinary applications are contemplated by the present disclosure. Human patients can be adult humans or juvenile humans (e.g., humans below the age of 18 years old). In addition to humans, patients include but are not limited to mice, rats, hamsters, guinea-pigs, rabbits, ferrets, cats, dogs, and primates. Included are, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 5C. Mean duration (length) of NREMS episodes before (white) and after nerve injury (filled).

FIG. 5D. Number of NREMS episodes before (white) and after the injury (filled).

FIG. 7A. Mice that express the light chain of the tetanus toxin in a Cre-recombinase-dependent manner were crossed with animals expressing this enzyme under the promoter of $Na(v)1.8$, a sodium channel mostly expressed in small-diameter (C-fibers) and medium-diameter (A-delta fibers) sensory neurons.

FIG. 7B. Wildtype mice developed NREMS fragmentation after nerve injury.

FIG. 7C. Mice whose A-delta and C pain fibers were genetically silenced did not develop sleep fragmentation after nerve injury.

FIG. 8E. Mean duration of wake, NREMS, and REMS in pre-SNI mice (first bar), SNI mice treated with saline (second bar), and SNI mice treated with carbamazepine (5 mg/kg; third bar).

FIG. 8F. Bout number of wake, NREMS, and REMS in pre-SNI mice (first bar), SNI mice treated with saline (second bar), and SNI mice treated with carbamazepine (5 mg/kg; third bar).

FIG. 8G. Percentages of wake, NREMS, and REMS in pre-SNI mice (first bar), SNI mice treated with saline (second bar), and SNI mice treated with carbamazepine (5 mg/kg; third bar).

DETAILED DESCRIPTION

Figure 1A:
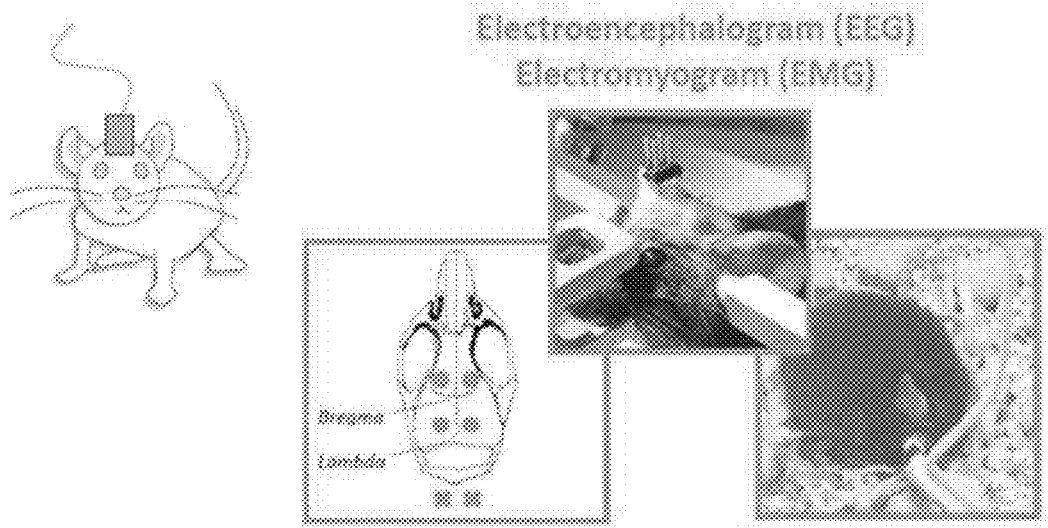
FIG. 1A. Surgical procedure to record electroencephalogram/electromyogram (EEG/EMG) in mice.

Pain is a sensory disturbance that is very difficult to measure accurately based on patient's subjective reports. There is a need for objective and sensitive biomarkers of pain—especially for the development of novel analgesics and also for clinically assessing the presence, extent and change in of pain in individual patients. There are arguably no good biomarkers for neuropathic pain at present. While functional imaging (e.g., magnetic resonance imaging) has been used to measure experimental induced and chronic pain, magnetic resonance imaging is very expensive, cannot be widely used to measure pain in the clinic or in a pre-clinical setting, has limited temporal resolution and cannot differentiate pain of neuropathic or other origin.

This disclosure provides biomarkers of a specific subset of neuropathic pain (e.g., spontaneous neuropathic pain). The present disclosure shows that neuropathic pain can causes a significant increase in brief awakenings (BAs) that can be detected by using polysomnography. These BAs are characterized by abrupt changes in EEG frequencies (indicating an awake state, which may include e.g., increase in theta and frequencies greater than 8 Hz) and brief increases in EMG amplitude that last less than 30 s. The brief awakenings disrupt sleep continuity and cause sleep fragmentation. The disclosure shows that an abnormal degree of sleep fragmentation can be detected in mice where they have pain hypersensitivity after nerve injury. Furthermore, the sleep fragmentation resolves when the evoked pain hypersensitivity returns to pre-injury (normal sensitivity) values (i.e. when the neuropathic pain has resolved). Therefore, the ectopic bursts of spontaneous activities of injured and neighboring non-injured sensory neurons from a lesioned nerve, which cause paroxysmal spontaneous neuropathic pain when a subject is awake, is also the underlying reason for excessive sleep fragmentation. Sleep fragmentation can thus be used as an objective, accurate and sensitive biomarker of neuropathic pain (e.g., spontaneous neuropathic pain). In some embodiments, the brief awakenings can be detected by an increase in respiration (e.g. rate, volume or $O_2$ levels measured by oximetry) or electrocardiogram (EKG) activity (e.g. increased heart rate) in combination with EEG/EMG While it is generally recognized that ongoing pain (or pain hypersensitivity) can cause difficulties to fall asleep (insomnia), BAs as described in the present disclosure are different from the state of wakefulness during insomnia, because BAs occur during and disrupt NREMS, and the subjects who experience BAs usually cannot recognize it or remember it. BAs are transient and generally do not cause behavioral awakening. They can reoccur several times per minute. The duration of these transient episodes of wake is also very short (e.g., less than 30 seconds). In contrast, the state of wakefulness (e.g., during insomnia) does not disrupt NREMS but prevent it from happening. The subjects, who are in the state of wakefulness during insomnia, can recognize that they are awake and can remember such experience. The period of the state of wakefulness during insomnia can be more than several minutes, half an hour, or even several hours. Insomnia caused by ongoing pain is an extension of daily wakefulness, while BAs caused by peripheral nerve injury disrupt NREMS. Peripheral nerve injury does not delay the NREMS onset in mice (i.e. no insomnia is generated). Importantly, BAs result in fragmented sleep rather than shortened sleep time.

Therefore, an increase in sleep fragmentation by BAs beyond normal physiological levels (baseline) can be used as biomarkers for the presence of neuropathic pain (e.g., spontaneous neuropathic pain). These biomarkers can have various applications, including, e.g., identifying new biological targets of neuropathic pain treatment, objectively measuring neuropathic pain in patients, and/or testing the efficacy of various drugs for treating neuropathic pain in clinical trials or in preclinical studies.

Pain

Pain is an unpleasant sensory and emotional experience. It is often associated with actual or potential tissue damage or can be described in terms of such damage. The feeling of pain is subjective. However, inability to verbally describe pain does not mean that an individual is not experiencing pain. Pain can be transitory or chronic. For example, transitory pain can last a few seconds, a few hours, or until the noxious stimulus is removed. Chronic pain, such as that associated with rheumatoid arthritis, peripheral neuropathy, trauma to the nervous system, cancer and idiopathic pain, can persist for years.

There are three currently known classes of pain: (1) nociceptive pain, which is a high-threshold pain caused by intense (noxious) stimuli (known as "protective pain"); (2) inflammatory pain, which is associated with tissue damage and infiltration of immune cells; and (3) pathological pain, which is a disease state caused by damage to or abnormal function of the nervous system (e.g. fibromyalgia, peripheral neuropathy, tension type headache, etc.). (Woolf, Clifford J. "What is this thing called pain?" The Journal of clinical investigation 120.11 (2010): 3742-3744).

Neuropathic pain is pain caused by damage or disease affecting the somatosensory nervous system. Patients with neuropathic pain can experience abnormal evoked pain sensations such as hyperalgesia (increased pain to a noxious stimulus), allodynia (pain felt in response to normally non-painful stimulations), and/or spontaneous pain. Spontaneous neuropathic pain is pain experienced in the absence of a stimulus. It typically can either be paroxysmal (bursts of short-lasting pain—typically electric shock like) or ongoing (commonly described as a burning sensation). Spontaneous neuropathic pain is a major complaint of patients with neuropathic pain and there are no preclinical or clinical objective measures of spontaneous neuropathic pain at this moment.

The present disclosure provides methods of objectively measuring neuropathic pain, particularly spontaneous neuropathic pain.

Non-Rapid Eye Movement Sleep (NREM) and Rapid Eye Movement Sleep (REMS)

Sleep is characterized by altered consciousness, relatively inhibited sensory activity, inhibition of nearly all voluntary muscles, and/or reduced interactions with surroundings. It occurs in repeating periods, in which the body alternates between two distinct modes: rapid eye movement sleep (REMS) sleep and non-rapid eye movement sleep (NREMS). REMS and NREMS alternate within one sleep cycle, which lasts about 90 minutes in adult humans. As sleep cycles continue, each sleep cycle shifts towards a higher proportion of REMS.

The REMS and NREMS can be detected by electroencephalogram (EEG), electromyogram (EMG), or both. EEG is an electrophysiological monitoring method to record electrical activity of the brain. It is typically noninvasive, with the electrodes placed along the scalp in humans. It measures voltage fluctuations resulting from ionic current within the neurons of the brain. These voltage fluctuations are recorded as brain waves. The brain waves are divided into four major groups based on frequency range. They include, e.g., delta waves (<4 Hz), theta waves (4~7 Hz), alpha waves (8~13 Hz), beta waves (13~30 Hz), and gamma waves (30~100 Hz), etc.

The electromyography (EMG) can also be used to characterize sleep. EMG records the electrical activity produced by skeletal muscles. It is often detected by an electromyography. The electromyography records the electric potential generated by muscle cells when these cells are electrically or neurologically activated. During REMS, the body is effectively completely paralyzed. However, during NREMS, the body does make some limited movements. This can be captured by EMG The EEG and EMG can be used together to characterize sleep. During REMS, the body is paralyzed, however the brain is similar to the state of wakefulness. EEG during REMS often records fast, low amplitude, desynchronized neural oscillation (brain waves) that resemble the pattern seen during wakefulness. This is different from the delta wave that can be seen during NREMS. REMS also is characterized by random/rapid movement of the eyes, accompanied with low muscle tone throughout the body.

During NREMS, there is usually little or no eye movement. NREMS can be divided into three stages. During Stage 1, alpha wave disappears and the theta wave appears. During Stage 2, EEG recordings tend to show characteristic "sleep spindles" (i.e., short bursts of high frequency brain activity), and "K-complexes" during this stage. During Stage 3, delta wave, which is associated with "deep" sleep, becomes more prominent.

How to distinguish wakefulness, REMS, and NREMS by brain waves is known in the art, and is described, e.g., Wolpert, Edward A. "A Manual of Standardized Terminology, Techniques and Scoring System for Sleep Stages of Human Subjects." Archives of General Psychiatry 20.2 (1969): 246-247; US 20040077967; US20100063349; US20090076407, each of which is incorporated by reference herein. Table 1 summarizes characteristic brain waves for the state of wakefulness, REMS and NREMS.

or a subject receiving innocuous (touch) stimuli. The BAs are characterized by high-frequency low amplitude EEG signals and a simultaneous increase of EMG tone. BAs are typically preceded by at least 10 seconds of continuous NREMS.

In some embodiments, the period of BAs can be shorter than 60, 50, 40, 30, 25, 24, 23, 22, 21, 20, 19, 18, 17, 16, 15, 14, 13, 12, 11, or 10 seconds. In some embodiments, the period of BAs can last more than 1, 2, 3, 4, or 5 seconds. In some embodiments, the period of BAs can last e.g., from 2 to 30 seconds, from 2 to 20 seconds, or from 2 to 15 seconds.

Because neuropathic pain can cause a significant increase of BAs, the frequency of BAs and/or the total number of BAs in a predetermined period can indicate the severity of neuropathic pain. Similarly, the total number of NREMS episodes in a predetermined period is also correlated with the severity of neuropathic pain. Because BAs disrupt NREMS, the average duration of NREMS episodes is also negatively correlated with the severity of neuropathic pain.

Thus, in some embodiments, the methods as described herein involve detecting an increase in frequency of BAs during sleep of the subject as compared to a reference level.

TABLE 1

| | Brain Waves | | | |
|---|---|---|---|---|
| Sleep Stage | Defining EEG Frequency | Type | Characteristics | Comments |
| Alert wakefulness | Fast, with many waves >13 Hz | Beta | Low voltage, random pattern, with few rhythmic components | |
| Relaxed wakefulness | 8-13 Hz | Alpha | Low voltage, rhythmic alpha, with occasional bursts of the alertness pattern | |
| NREMS N1 | 4-7 Hz | Theta | Theta waves interspersed with brief periods of alpha waves | Reactivity to outside stimuli diminishes; sleepers may still feel awake |
| NREMS N2 | 12-14 lasting >0.5 seconds. Isolated slow/ high amplitude waves | Theta with sleep spindles and K-complexes | At least 1 sleep spindle or K-complex per 30 seconds on a N1 back-ground | The most prominent sleep stage, deeper than N1 sleep, lighter than N3 sleep |
| NREMS N3- Slow Wave Sleep (SWS) | <4 Hz | Delta | High amplitude, low waves | Deepest sleep; duration of SWS depends on age (less in the elderly) |
| REMS | N1 pattern with "saw tooth waves" | Low voltage, random, fast | Eyes move; the autonomic system is activated (e.g., respiratory and cardiac irregularities). | A unique state, in which dreams usually occur. The brain is awake & body paralyzed (REM-related atonia). |

Biomarkers for Neuropathic Pain

The present disclosure describes methods of objectively measuring neuropathic pain in a subject using various biomarkers. In one aspect, the methods involve using EEG recordings, EMG recordings, or the combination of both, e.g., before and/or after nerve injury.

The present disclosure shows that neuropathic pain (e.g., spontaneous neuropathic pain) can cause excessive fragmentation of NREMS, which is disrupted by an abnormal level of BAs. The degree of fragmentation can be much higher than the degree of fragmentation in a normal subject The reference level can be, e.g., the average frequency of BAs in subjects who do not suffer from pain (e.g., neuropathic pain) or report to suffer from pain, or the average frequency of BAs in the subjects before any injury or before experiencing any pain (e.g., neuropathic pain). In some embodiments, the increase can be at least 10%, 20%, 30%, 40%, 50%, 60%, 70%, 80%, 90%, 100%, 150%, or 200% more than the reference level.

In some embodiments, the frequency of BAs is measured by the number of BAs in a predetermined period (e.g., one day (in individuals/animals who sleep during the day), one night, the entire sleep period at night, twelve hours, six hours, five hours, four hours, three hours, two hours, one hour, thirty minutes or one minute). In some embodiments, the average BAs in healthy human subjects is about 6, 7, 8, 9, 10, 11, 12, 13, 14, 15, 16, 17, 18, 19, 20, 21, 22, 23, 24, or 25 BAs per hour.

In some embodiments, the methods involve detecting an increase in the total number of BAs in a predetermined period as compared to a reference level. The reference level can be, e.g., the total number of BAs in subjects who do not suffer from pain (e.g., neuropathic pain) or report to suffer from pain in the predetermined period, or the total number of BAs in the subjects before any injury. In some embodiments, the increase can be at least 10%, 20%, 30%, 40%, 50%, 60%, 70%, 80%, 90%, 100%, 150%, or 200% more than the reference level.

In some embodiments, the predetermined period is one day (e.g., in individuals/animals who sleep during the day), one night, or the entire sleep period at night. In some embodiments, the length of the predetermined period is 1, 2, 3, 4, 5, 6, 7, 8, 9, 10, 20, 30, 40, 50, 60 minutes. In some embodiments, the length of the predetermined period is 1, 2, 3, 4, 5, 6, 7, 8, 9, 10, 11, 12, 13, 14, 15, 16, 17, 18, 19, 20, 21, 22, 23, or 24 hours. In some embodiments, the predetermined period is the total sleep time of the subject within 24 hours. In some embodiments, the predetermined period is the total sleep time during one night. In some embodiments, the predetermined period starts after 7:00 PM, 8:00 PM, 9:00 PM, 10:00 PM, 11:00 PM, and/or ends before 6:00 AM, 7:00 AM, 8:00 AM, 9:00 AM, or 10:00 AM the next day.

As BAs disrupt NREMS, an increase of the number of NREMS episodes is also associated with the severity of neuropathic pain. Thus, in some embodiments, the methods as described herein involve detecting an increase in the number of NREMS during sleep as compared to a reference level. The reference level can be, e.g., the average number of NREMS in subjects who do not suffer from pain (e.g., neuropathic pain) or report to suffer from pain, or the average number of NREMS in the subjects before any injury or before experiencing any pain. In some embodiments, the increase can be at least 20%, 30%, 40%, 50%, 60%, 70%, 80%, 90%, 100%, 150%, or 200% more than the reference level.

Similarly, because BAs disrupt NREMS, the average length of NREMS episodes will be shortened accordingly. Thus, in some embodiments, the methods as described herein involve detecting a decrease in the mean duration of NREMS episodes as compared to a reference level. The reference level can be, e.g., the average duration of NREMS in subjects who do not suffer from pain (e.g., neuropathic pain) or report to suffer from pain, or the average duration of NREMS episodes in the subjects before any injury to the nervous system. In some embodiments, the decrease can be more than, 20%, 30%, 40%, or 50% of the reference level.

In some embodiments, the reference level is a predetermined threshold. Thus, if the frequency of BAs, the number of BAs in a predetermined period, the number of NREMS episodes in a predetermined period is greater than the reference level, or the average duration of NREMS episode is shorter than the reference level, then it can be determined that the subject experiences neuropathic pain (e.g., spontaneous neuropathic pain).

Pain Treatment

The present disclosure provides methods of treating neuropathic pain (e.g., spontaneous neuropathic pain). The methods involve objectively determining that a subject experiences neuropathic pain (e.g., by detecting an increase in frequency of BAs, a decrease in average duration of NREMS episodes, or an increase in the number of BAs etc.), and administering to the subject an analgesic agent.

Many different classes of analgesic agents are useful for treating neuropathic pain, including e.g., narcotic analgesic agents, anticonvulsant agents (e.g. anti-epileptic compounds), corticosteroids, secondary amine tricyclic antidepressants (TCA) (e.g., nortriptyline, or desipramine), selective serotonin norephinephrine reuptake inhibitors (SSNRI) (e.g., duloxetine, venlafaxine), calcium channel a2-d ligands (e.g., gabapentin, pregabalin or other gabapentanoids), N-methyl-D-aspartate (NMDA) receptor antagonists (e.g., dextromethorphan or memantine), sepiapterin reductase inhibitors, dual amine uptake inhibitors, sodium channel blockers, GABA enhancers, potassium channel openers, microglial inhibitors, calcium channel blockers, Electroneutral Potassium-Chloride Cotransporter 2 (KCC2) activators, or any combination thereof.

In some embodiments, the analgesic agent is a narcotic analgesic agent (e.g., opioids). Morphine, the archetypal opioid, and other opioids (e.g., codeine, oxycodone, hydrocodone, dihydromorphine, pethidine) all exert a similar influence on the cerebral opioid receptor system.

In some embodiments, the analgesic agent is an anticonvulsant agent. As used herein, the term "anticonvulsant agent" refers to the group of medications that work to relieve neuropathic pain. These medications can alter the function of the injured nerve or central nervous system and the signals that are sent to the brain. Some common anticonvulsant agents include, e.g., Gabapentin, Pregabalin, and carbamazepine. The present disclosure shows these anticonvulsant agents (e.g. anti-epileptic compounds) are effective for treating neuropathic pain. These agents can restore normal sleep in injured mice at doses that do not cause sedation. Thus, the present disclosure also provides methods of treating neuropathic pain, wherein the medication does not cause sedation.

In some embodiments, the analgesic agent is a corticosteroid. Corticosteroids are powerful anti-inflammatory medications, and can be used for acute pain or for flare-ups of a chronic neuritis.

In some embodiments, the analgesic agent is a secondary amine tricyclic antidepressant (TCA). Tricyclic antidepressants are a class of medications that are used primarily as antidepressants. The secondary amines TCAs include e.g., desipramine, nortriptyline, protriptyline, etc.

In some embodiments, the analgesic agent or treatment is amitriptyline, alfentanil, almotriptan, buprenorphine, butalbital, butorphanol, carbamazepine, codeine, diflunisal, dihydrocodeine, diphenhydramine, eletriptan, ergotamine, fentanyl, frovatriptan, fluoxetine, gabapentin, hydrocodone, hydromorphone, imipramine, isometheptene mucate, levorphanol, mexiletine, meperidine, methadone, morphine, nalbuphine, naratriptan, oxycodone, oxymorphone, phenyltoloxamine, piroxicam, propoxyphene, rizatriptan, sumatriptan, tapentadol, tolmetin, tramadol, ziconotide, or zolmitriptan, or any combination thereof.

In some embodiments, the analgesic agent or treatment is topical lidocaine (5%), Carbamazepine, Lacosamide, Lamotrigine, Oxcarbazepine, Topiramate, Valproate, sulfasalazine, capsaicin (1-8%) patches or cream, Tetrahydrocannabinol, botulin toxin, sepiapterin reductase inhibitors or other compounds that reduce tetrahydrobiopterin production.

In some embodiments, the analgesic agent is an anti-nerve growth factor (NGF) antibody.

In some embodiments, the treatment is any interventional therapy that can modulate central nervous system, e.g.

stimulation of the CNS (peripheral nerves, spinal cord, or brain). In some embodiments, the treatment is a surgical approach.

In addition, local anesthetics can provide temporary pain relief to an area. When used in the setting of chronic neuropathic pain, local anesthetics are often applied as a regional injection to the injured nerve.

Because many of these analgesic agents or treatments have side effects, these analgesic agents or treatments should be administered to a subject who is actually experiencing neuropathic pain, or at least the dosage should be limited to an appropriate level. Thus, in some other settings, the methods as described herein can be used to adjust treatment for a subject having neuropathic pain. For example, the dosage can be increased if the treatment is not effective (e.g., the frequency of BAs is still higher than the reference level after the initial treatment). Similarly, the dosage can be decreased or not changed if the treatment is effective (e.g., the frequency of BAs is lower than the reference level or comparable to the reference level).

In some other embodiments, if it has been determined that a subject does not actually experience neuropathic pain or the neuropathic pain experienced by the subject has not reached to a threshold level, the pain treatment can be withheld from the subject.

As different pain conditions have different causes, they may require different medications. Also provided are methods of adjusting treatment for a subject having neuropathic pain. The methods can involve administering a first analgesic agent to a subject; determining whether the first analgesic agent is effective; continuing treating the subject with the first analgesic agent if it is effective; or administering to the subject a second, different type of analgesic agent if the first analgesic agent is not effective.

Furthermore, the methods as described herein can be used to determine whether a subject is/has experienced neuropathic pain, wherein the subject, for any reason, cannot articulate or indicate that the subject is experiencing neuropathic pain. For example, the subject can be an infant (e.g., less than 3, 4, 5, 6, 7, 8, 9, 10, 11, or 12 months old), a person with disabilities, a person with limited language ability, a person that speaks a foreign language, or a comatose or unconscious patient. In some embodiments, the subject is a non-human animal (e.g., mice).

Methods of Screening

Included herein are methods for screening or testing test compounds, e.g., polypeptides, polynucleotides, inorganic or organic large or small molecule test compounds, to identify agents that are useful and effective for treating neuropathic pain (e.g., spontaneous neuropathic pain).

The methods can involve, e.g., administering a test agent to a subject; determining whether the test agent is effective for treating neuropathic pain; and identifying the test agent as an analgesic agent for treating neuropathic pain. For example, if the subject has a decrease in frequency of BAs during sleep, a decrease in the total number of BAs in a predetermined period, a decrease in the number of NREMS episodes, and/or an increase in average duration of NREMS episodes, the test agent is an effective analgesic agent for treating neuropathic pain. In some embodiments, the subject is a non-human animal (e.g., mice). In some other embodiments, the subject is a human (e.g., a human subject in clinical trials).

The methods can be used to identify treatments (e.g., any interventional therapy that can modulate central nervous system such as surgeries) that are useful and effective for treating neuropathic pain. The methods can involve, e.g., administering the therapy (e.g., performing a surgery) to the subject, and measuring the frequency of BAs, the total number of BAs in a predetermined period, the number of NREMS episodes, and/or the average duration of NREMS episodes.

Treatment, screening, and/or manufacturing methods described herein may involve small molecules. As used herein, "small molecules" refers to small organic or inorganic molecules of molecular weight below about 3,000 Daltons. In general, small molecules useful for the methods described herein have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, Solid-Supported Combinatorial and Parallel Synthesis of Small-Molecular-Weight Compound Libraries, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available.

Libraries screened using the methods of the present disclosure can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

Thus, test compounds identified as "hits" (e.g., test compounds that are effective for treating neuropathic pain) in a first screen can be selected and systematically altered, e.g., using rational design, to optimize binding affinity, avidity, specificity, or other parameter. Such optimization can also be screened for using the methods described herein. Thus, in one embodiment, the disclosure includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating neuropathic pain. A variety of techniques useful for determining the structures of "hits" can be used in the methods described herein, e.g., NMR, mass spectrometry, gas chromatography equipped with electron capture detectors, fluorescence and absorption spectroscopy.

Medication Dispensing System

The methods as described herein can be used in a number of clinical settings. Most commonly, physicians and other health care professionals can apply these methods described herein to diagnose and/or treat a patient. Physicians may use these methods to track the progress of a patient's illness over time or to determine an amount of pain medication to prescribe to a patient. In other settings, these methods may be used to test the efficacy of certain known pain-relieving drugs or dugs whose pain-relieving effects are being investigated for the first time and to establish standard dosages for them.

Pain assessment plays a vital role in determining the amount of pain medication to give a patient. The present disclosure provides an objective way to measure neuropathic pain experienced by the subject. The neuropathic pain can be detected by EEG, EMG, or both. Thus, the disclosure provides a medication dispensing system, in which the neuropathic pain of the patient can be detected by the system, and the system can administer or provide to the patient an appropriate dose of medication, e.g., automatically. In some embodiments, a machine learning algorithm can be used to determine the degree of neuropathic pain.

In some settings, hospitals and other healthcare often provide patients with Patient Controlled Analgesia (PCA) devices. PCA devices employ a type of analgesia system that enables the patient, often in a post-operative setting, to self-administer pain medicine. The PCA devices can also be used in connection with the methods as described herein. For example, when a patient falls asleep, the system can assess the degree of neuropathic pain, and can administer an appropriate medication or an appropriate dose to the patient to improve sleep quality.

Exemplary pain medication dispensing systems and PCA devices are described e.g., in U.S. Pat. Nos. 6,768,920, 8,920,382, US20070092858, US 20030204148 A1, US20130245605, which are incorporated herein by reference in the entirety.

EXAMPLES

The invention is further described in the following examples, which do not limit the scope of the invention described in the claims.

Example 1

Electroencephalogram/Electromyogram (EEG/EMG) Recordings in Mice

The following materials and methods were used in the following examples.

EEG/EMG implantation surgery: C57BL6/j mice were anesthetized with isoflurane gas (3% induction/2% maintenance) and placed in a stereotaxic apparatus (David Kopf Instruments, Tujunga, CA). As shown in FIG. 1A, four miniature stainless steel screws (Plastics One; 00-96 X 1/16) were positioned onto the dura through craniotomy holes for frontoparietal EEG recordings (AP: +2 mm, ML: ±2 mm and AP: −4 mm, ML: ±2 mm) and anchored to the skull with acrylic cement. Two flexible EMG electrodes(multistranded stainless steel wire; AS131, Cooner Wire, Chatsworth, CA) were inserted into the neck extensor muscles. All electrodes were previously soldered to a six-pin connector (MMX852-10-006-10-001000; Mill-Maz Mfg. Corp., Oyster Bay, NY) and covered with epoxy glue to ensure insulation. The headmount was affixed to the animal's skull with dental acrylic cement, and the scalp wound was sutured closed behind the headmount. Mice were given meloxicam (5 mg/kg, i.p.) before they regained consciousness and then daily for 3 days and were housed singly after surgery.

Figure 1B:
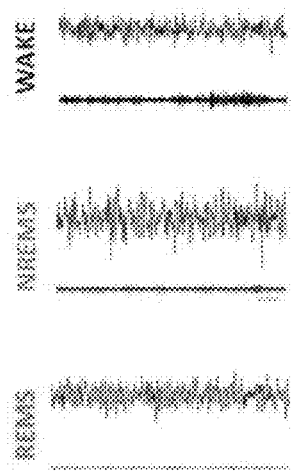
FIG. 1B. Examples of EEG (top trace) and EMG (bottom trace) signals for wake, Non-Rapid Eye Movement Sleep (NREMS) and Rapid Eye Movement sleep (REMS).
Figure 2:
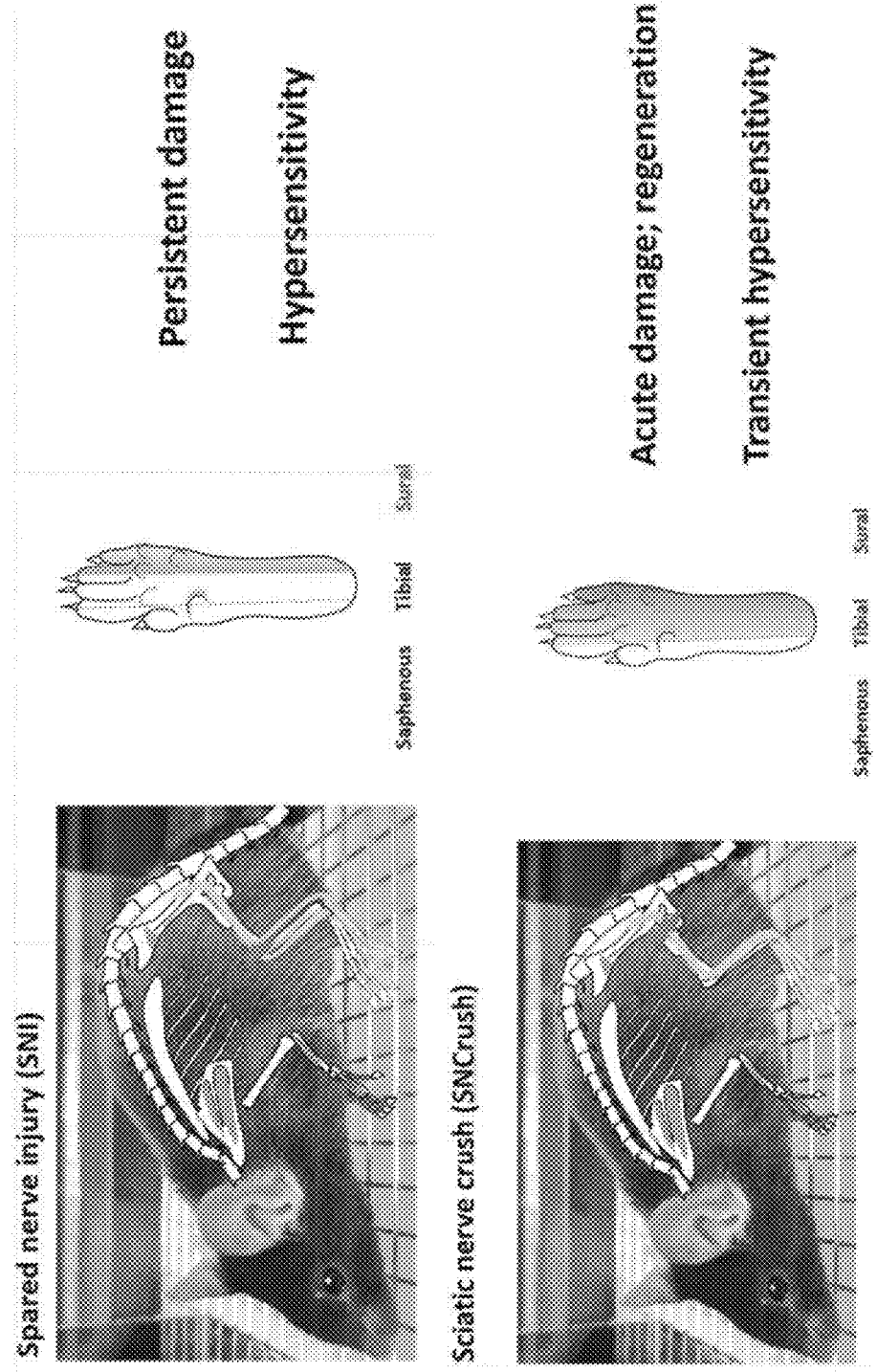
FIG. 2. Mouse models of neuropathic pain, including spared nerve injury (SNI) model and sciatic nerve crush (SNCrush) model.

EEG/EMG acquisition: Ten to fifteen days after EEG/EMG implantation, mice were transferred to individual sleep-recording cages (transparent cylindrical cage, 12" diameter and 12" height) in a sound-attenuated chamber with a 12:12 h light-dark cycle, ad libitum food and water, and connected to a tethered pre-amplifier (100× gain, 0.5 Hz high-pass filter for EEG, 10 Hz high-pass filter for EMG; Pinnacle Technology Inc., Lawrence, KS, USA). The other end of the tether was plugged into a low-torque commutator (8204, Pinnacle Technology Inc., Lawrence, KS, USA) for freely moving recordings. A data conditioning and acquisition system (DCAS, 8206) performed secondary amplification and filtering (low-pass filter: 100 Hz for EEG, 200 Hz for EMG). Mice habituated for 3-5 days to the recording setup before their baseline sleep-wake and sensory behaviors were measured. FIG. 1B shows some examples of traces for wake, Non-Rapid Eye Movement Sleep (NREMS) and Rapid Eye Movement sleep (REMS).

Example 2

Mouse Models of Neuropathic Pain

Spared nerve injury (SNI): surgery was performed under 3% induction/2% maintenance with isoflurane on adult mice (8 to 12 weeks old). The tibial and common peroneal branches of the sciatic nerve were tightly ligated with a 5.0 silk suture and transected distally, while the sural nerve was left intact (Decosterd and Woolf, 2000). After injury, incision was sutured and mice were allowed to recover on heated pads before being returned to their homecage. The surgeon who performed the SNI was blinded to the genotype. This model causes permanent pain hypersensitivity.

Sciatic nerve crush (SNcrush): surgery was performed under 3% induction/2% maintenance with isoflurane on adult mice (8 to 12 weeks old). The left sciatic nerve was exposed just below the sciatic notch under sterile conditions and then crushed using Dumont #5/45 forceps for 30 seconds under a dissection microscope. After the nerve injury, the incision wound was sutured and animals were allowed to recover on heated pads before being returned to their home cage. The surgeon who performed the SNcrush was blinded to the treatment. This model causes transient hypersensitivity before return to normal sensitivity.

Sham control: surgery was performed under 3% induction/2% maintenance with isoflurane on adult mice (8 to 12 weeks old). The left sciatic nerve was exposed but left intact and the animals were allowed to recover on heated pads before being returned to their home cage.

Example 3

Sleep Analysis and Brief Awakening (BA) Quantification

EEG and EMG signals were digitized at a sampling rate of 400 Hz through Sirenia® Acquisition software (Pinnacle Technology Inc, Lawrence, KS, USA) and converted to European Data Format (.EDF). Using SleepSign® for Animal (Kissei Comtec Co., Japan) software, EEG and EMG signals were digitally filtered (EEG, 0.5-100 Hz; EMG, 10-200 Hz) and scored semi-automatically using 10-s epochs, as wake, NREMS or REMS. This preliminary scoring was visually inspected by a trained experimenter, who was blinded to the experimental conditions, and corrected when appropriate. To evaluate sleep fragmentation, transient waking events occurring during NREMS were evaluated: these brief awakenings (BAs) were defined by a high-frequency low-amplitude EEG associated with an increase of EMG tone ranging from 2-15 s (Franken et al., 1991; Tobler et al., 1997).

For each pain condition and time-point, general sleep-wake architecture was assessed by calculating the percentage of time spent in wake, NREMS and REMS, as well as the number and mean duration of episodes for each state. The episode distribution for each state as a function of their duration was also analyzed.

Figures 3A, 3B, 3C:
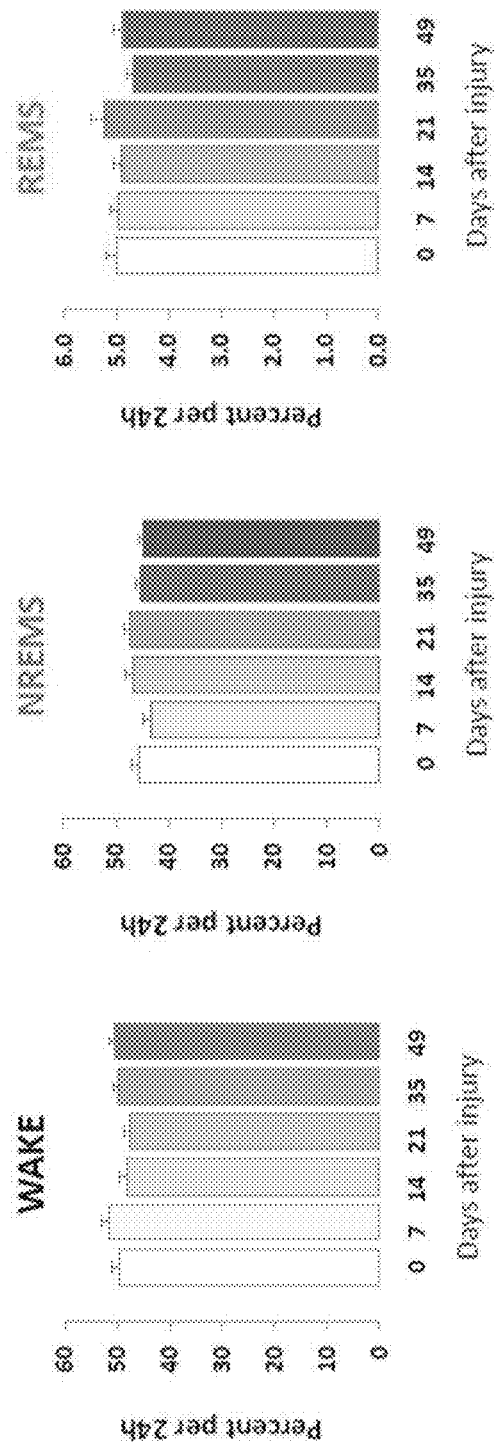
FIG. 3A. The percentage of wake time before and after nerve injury.
FIG. 3B. The percentage of NREMS time before and after nerve injury.
FIG. 3C. The percentage of REMS time before and after nerve injury.
Figure 3D:
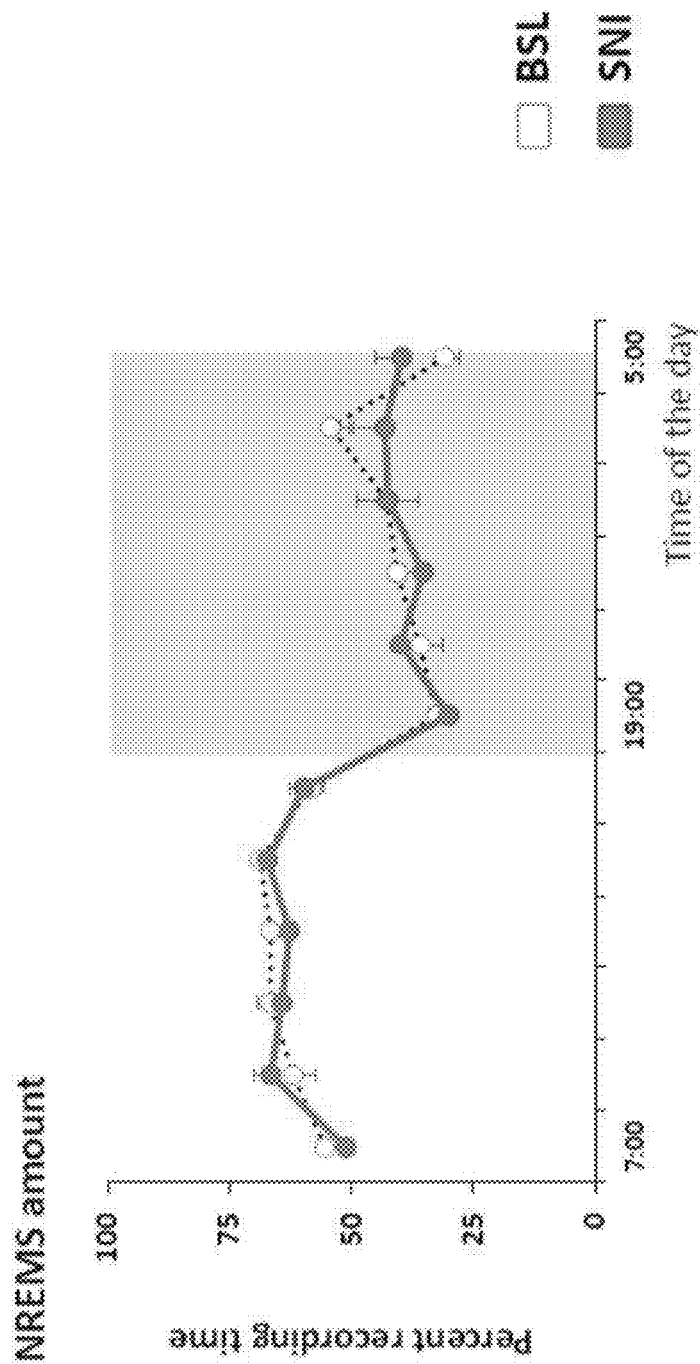
FIG. 3D. Circadian distribution of sleep was not altered after nerve injury.

As shown in FIGS. 3A-3C, the total wake, NREMS and REMS amount are not changed by nerve injury. FIG. 3D shows NREMS amount over 1 day before (BSL) and 14 days after injury (SNI). The results indicate that circadian sleep-wake behaviors of the mice were not altered after the injury.

Figure 4:
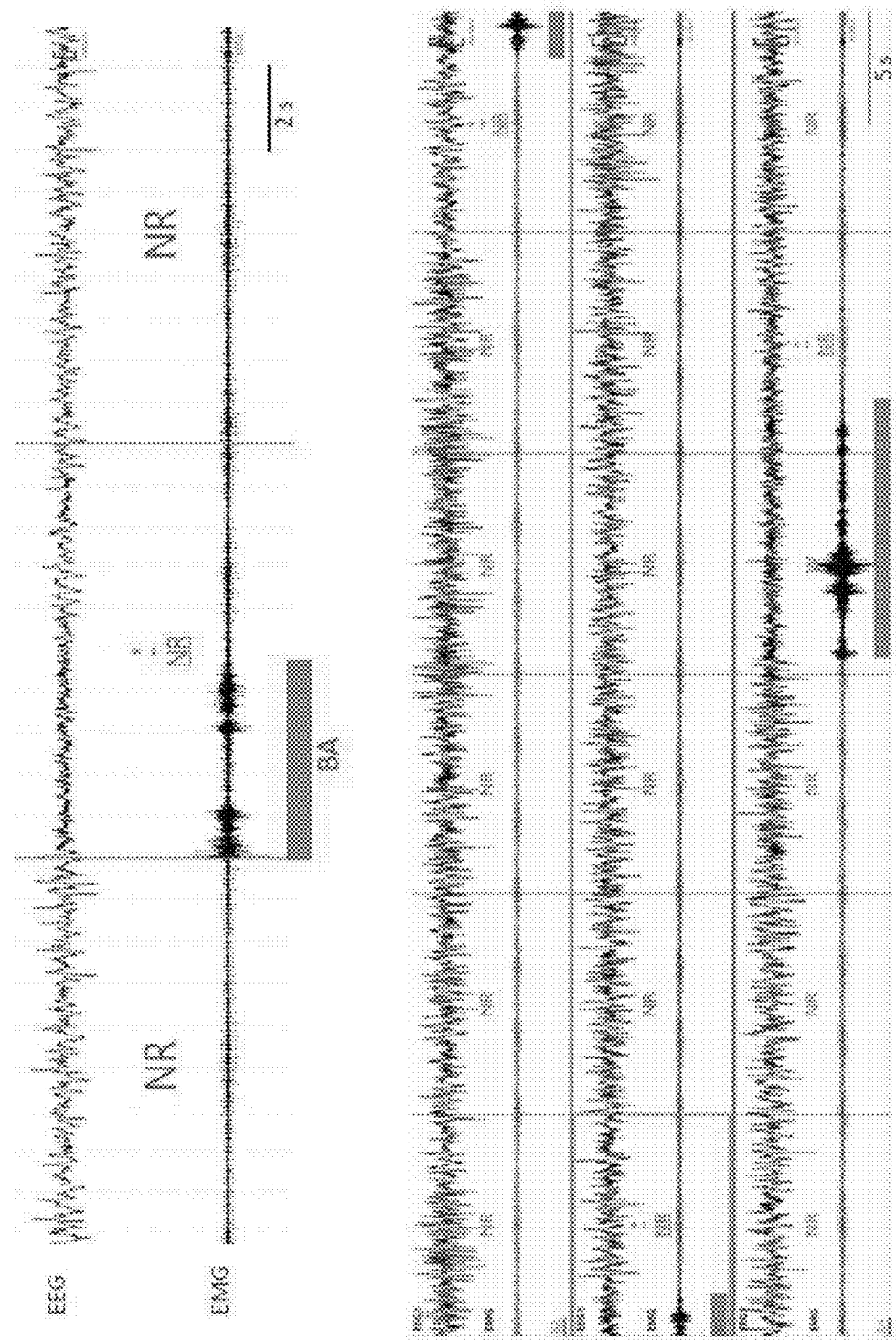
FIG. 4. Examples of scoring of brief awakenings (BA).

BAs was computed per minute or hour of NREMS. In FIG. 4, BAs were scored by a blinded experimenter and digitally "annotated" on the EEG trace (bar). The number of BAs was then calculated and computed per minute or hour of NREMS for each time interval. The nerve injury causes a significant 50% increase in brief awakenings (lasting 2 to 15 s) as detected by EEG/EMG recordings, that disrupts sleep continuity and causes sleep fragmentation.

Example 4

Peripheral Nerve Injury Fragments Sleep by Brief Awakenings (BAs)

Figure 5A:
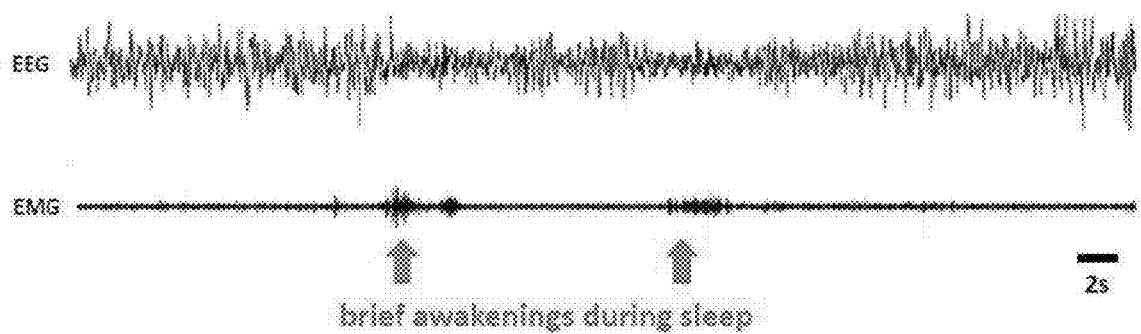
FIG. 5A. Example of EEG and EMG traces from a mouse 14 days after nerve injury.

FIG. 5A shows example of the EEG and EMG recordings from a mouse 14 days after nerve injury. As shown in the figure, two periods of brief awakenings disrupted sleep continuity.

Figure 5B:
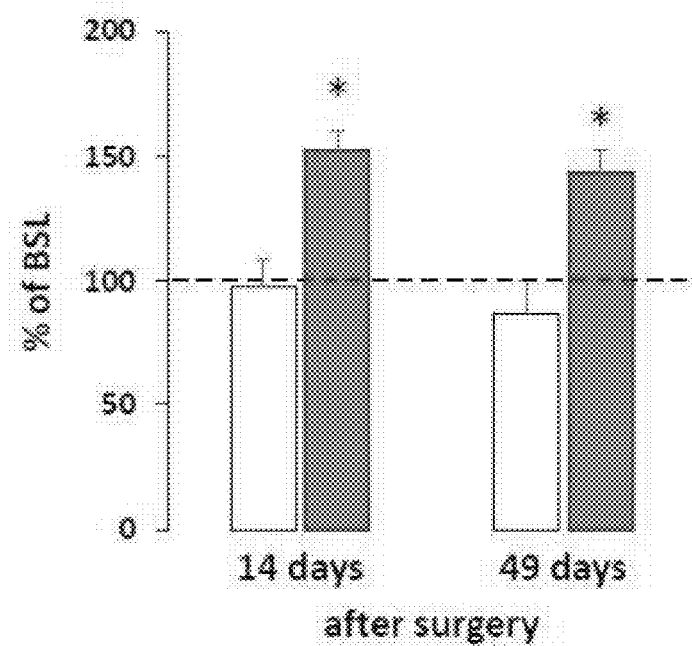
FIG. 5B. Quantification of the number of BAs in mice that after nerve injury (filled) or sham procedure (white), expressed as percentage of baseline (BSL, dashed line).

FIG. 5B shows quantification of the number of BAs in mice that received nerve injury (filled) or sham procedure (white) compared to their baseline value (dashed line).

As a result of BAs disrupting sleep, the duration of each NREMS episode is shortened (FIG. 5C) and the number of NREMS episode per day is increased (FIG. 5D). White bar are for the mice before injury. Filled bar are the results for the mice 14 days after SNI.

Example 5

Sleep Fragmentation by BAs Correlates With Abnormal Pain Sensitivity

Figures 6A, 6B, 6C:
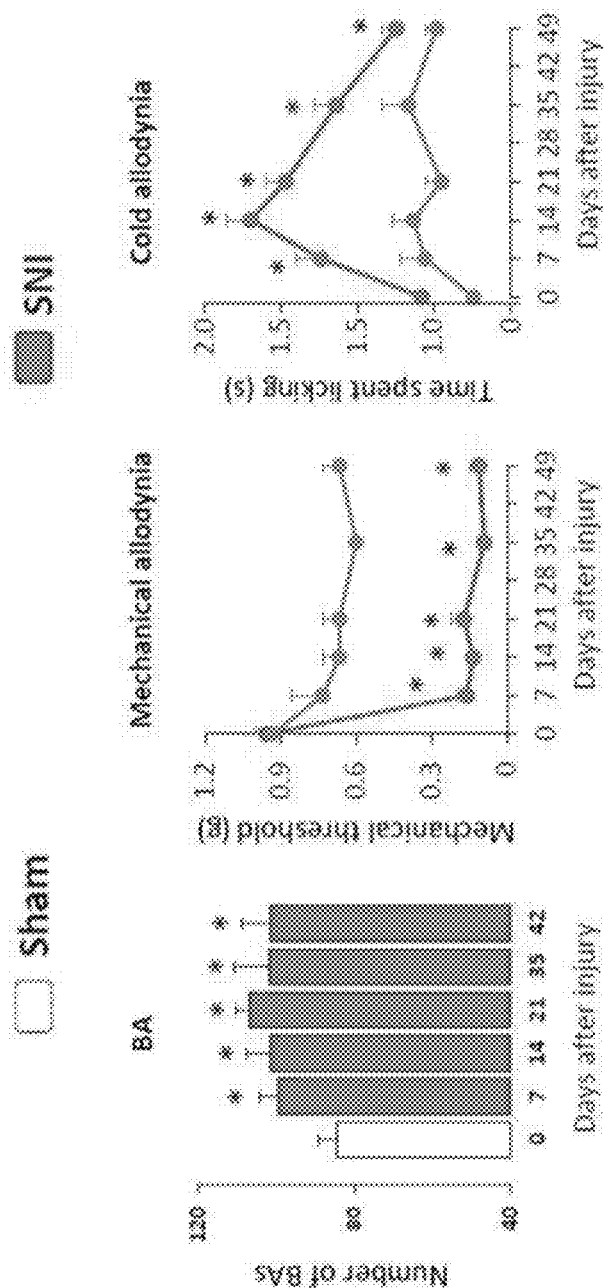
FIGS. 6A-6C. Number of BAs is increased only in mice that display abnormal pain hypersensitivity (SNI mice).

FIGS. 6A-6C. Number of BAs is increased only in mice that display abnormal pain hypersensitivity. FIG. 6B shows that SNI mice had a lower pain threshold in response to touching. When pain was induced by cold, SNI mice spent more time in licking, indicating a higher severity of pain (FIG. 6C).

Figures 6D, 6E, 6F:
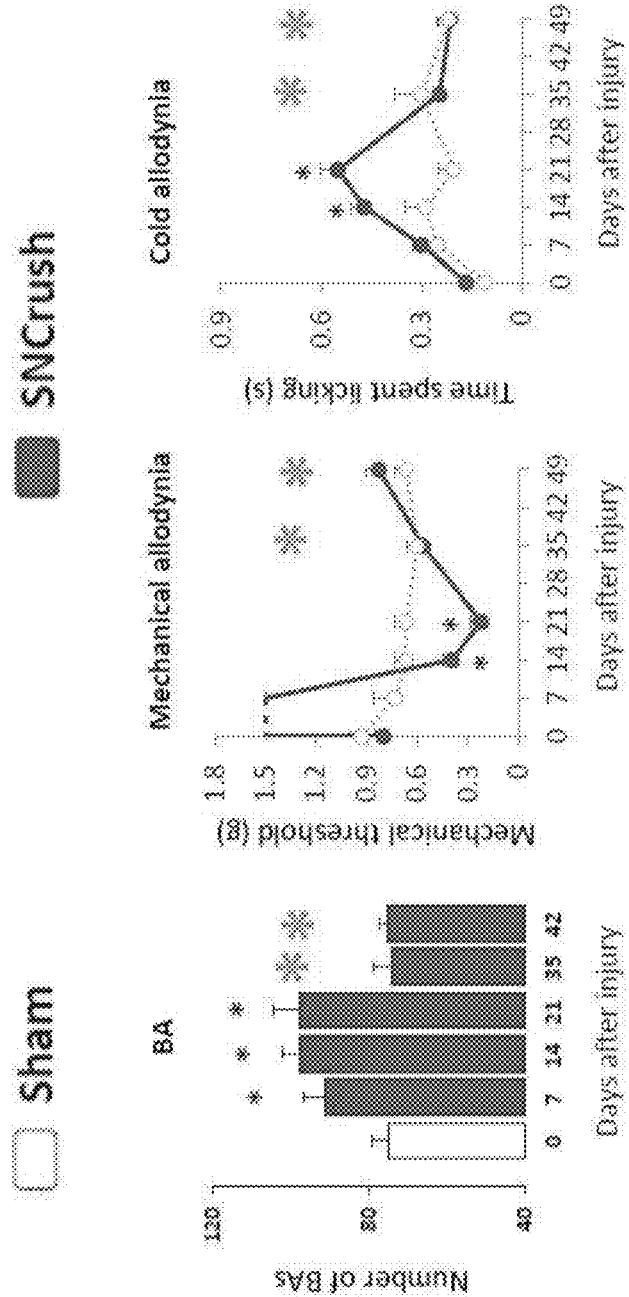
FIGS. 6D-6F. Sleep fragmentation occurred in mice with abnormal pain hypersensitivity, and resolved in animals that recovered normal sensitivity (indicated by stars).

FIGS. 6D-6E. As a result, sleep was fragmented in mice with abnormal pain hypersensitivity, and sleep fragmentation resolved in animals that recover normal sensitivity (indicated by stars in FIGS. 6D-6E).

Figure 6G:
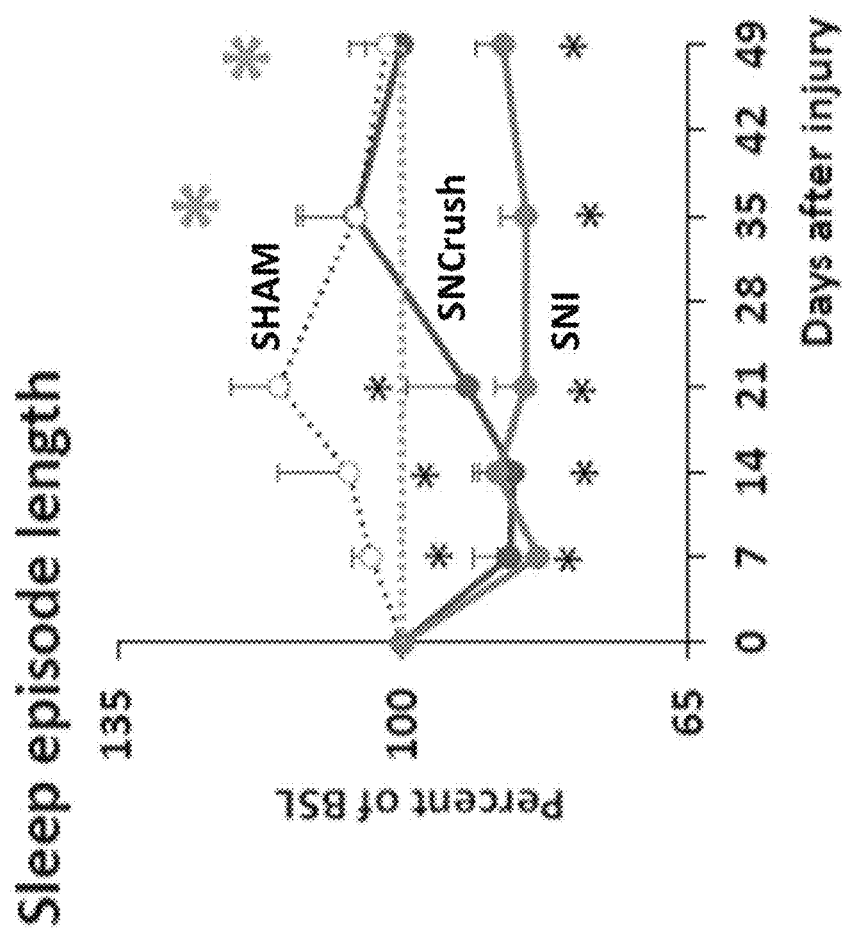
FIG. 6G. NREMS episode length in SNI, SNCrush, and sham mice.

Furthermore, when the animals recovered normal sensitivity, the sleep episode length also recovered to the normal level (FIG. 6G). In contrast, in SNI mice, the sleep episode length was not recovered to the normal level.

Example 6

BA are Caused by Ectopic Activity in Pain Fibers

Mice that express the light chain of the tetanus toxin in a Cre-recombinase-dependent manner were crossed with animals expressing this enzyme under the promoter of Na(v) 1.8, a sodium channel only present in medium diameter (As) and small diameter (C) sensory fibers (FIG. 7A). Cells producing the light chain of the tetanus toxin cannot perform exocytosis but remain otherwise alive, which leads to a sensory neuron-specific silencing.

Figures 7D, 7E:
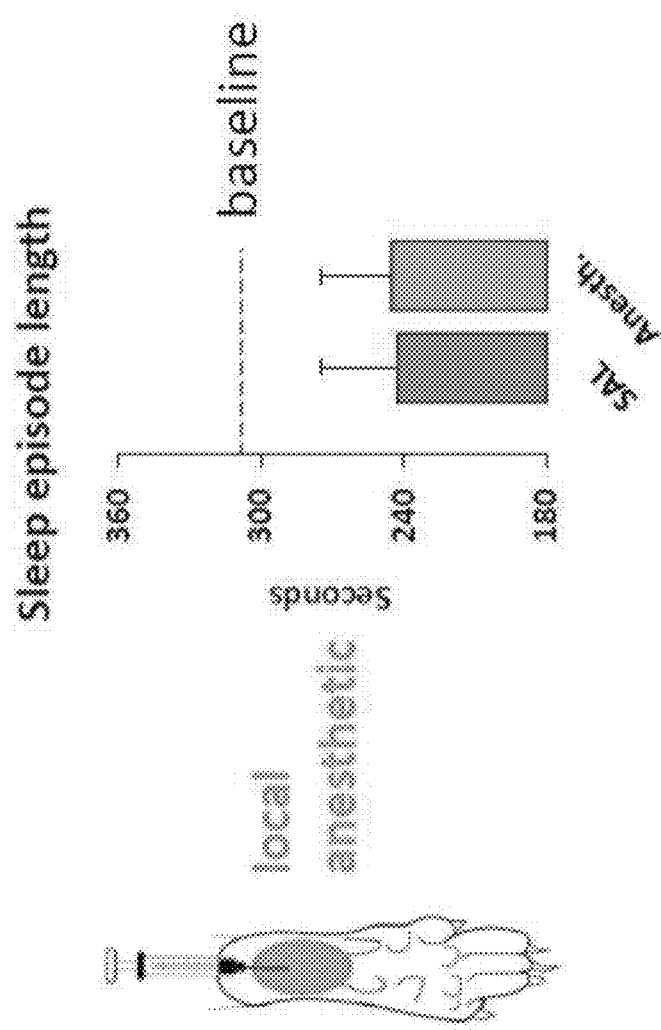
FIG. 7D is a graph showing the procedure for silencing peripheral nerve terminals (intraplantar injection of local anesthetic).
FIG. 7E. Silencing peripheral nerve terminals did not block NREMS fragmentation by BAs.

Mice whose pain fibers were genetically silenced did not develop sleep fragmentation after nerve injury compared to WT littermates (FIGS. 7B-7C). However, silencing peripheral nerve terminals did not block sleep fragmentation by BAs (FIGS. 7D-7E).

Thus, transgenic mice whose peripheral nociceptors (peripheral pain fibers) were genetically silenced (cannot activate neurons in the CNS) did not develop the sleep fragmentation after nerve injury, indicating that these neurons are the source of the input that causes the abnormal degree of sleep fragmentation. Silencing of nerve terminals with a local anesthetic did not restore normal sleep in SNI mice, indicating that peripheral stimuli (as may be caused by movement or contact with a surface) did not drive the activity in nociceptors.

Example 7

Analgesics Drugs (Gabapentin or Carbamazepine) Restored Normal Sleep Without Causing Sedation in SNI Mice Administration of analgesics drugs (gabapentin, carbamazepine) can dose-dependently normalize sleep fragmentation in mice with efficacy at doses active in patients with neuropathic pain.

Figure 8A:
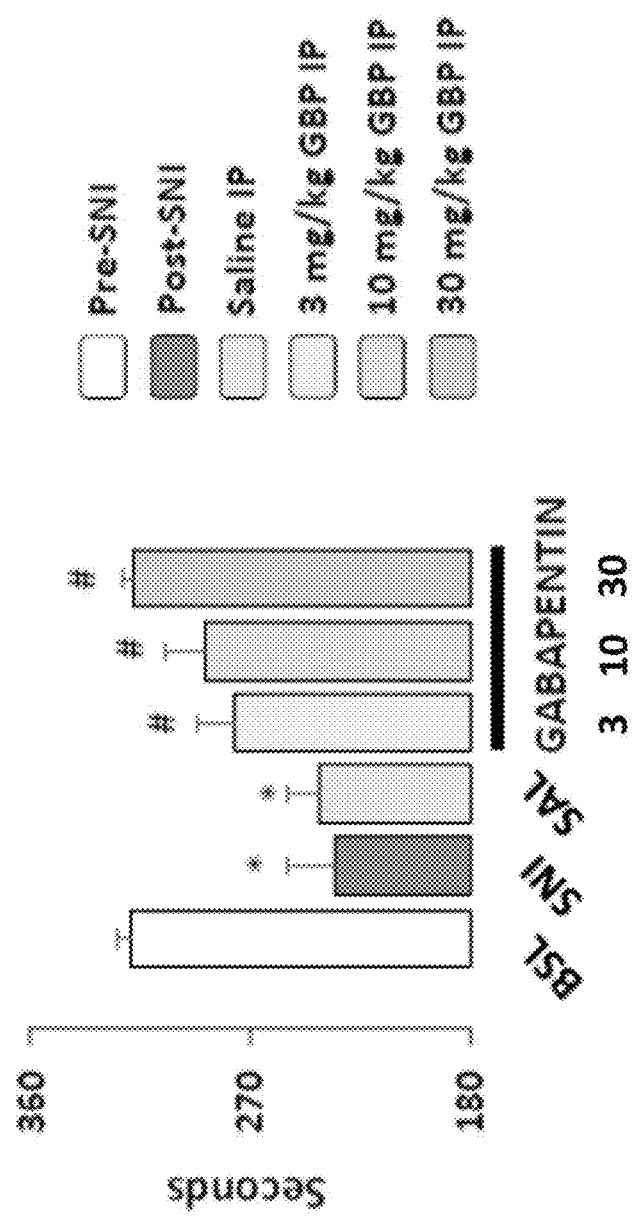
FIG. 8A. Length of NREMS episodes in SNI mice that were treated by gabapentin (GBP).
Figure 8B:
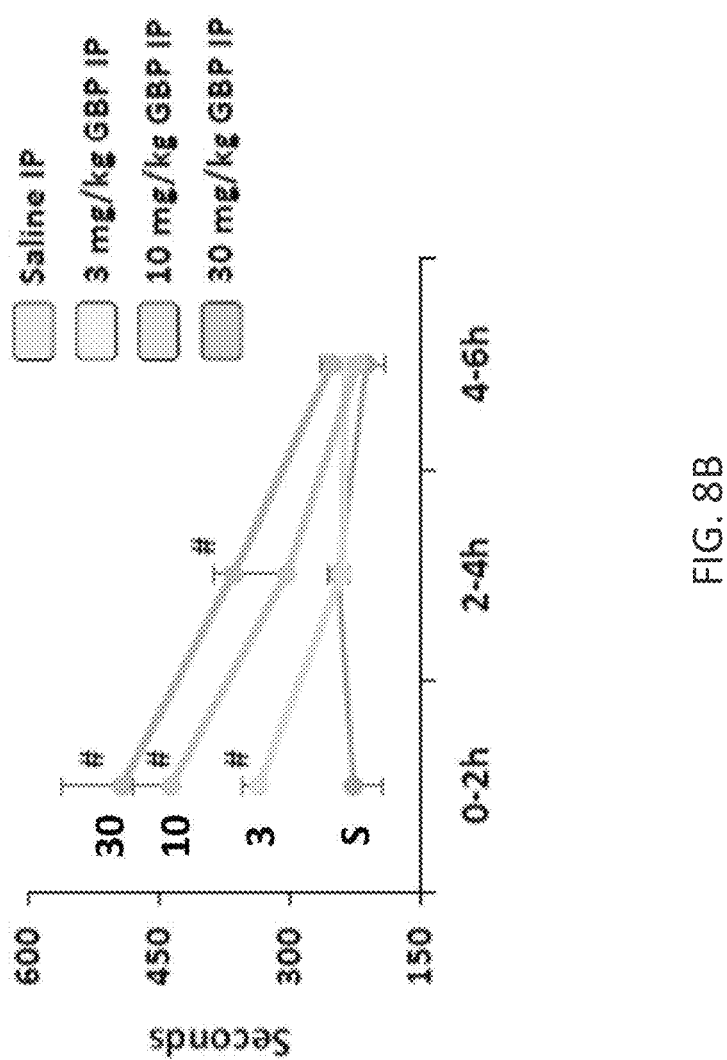
FIG. 8B. Length of NREMS episodes in SNI mice at different time points after being treated by gabapentin (GBP).
Figures 8C, 8D:
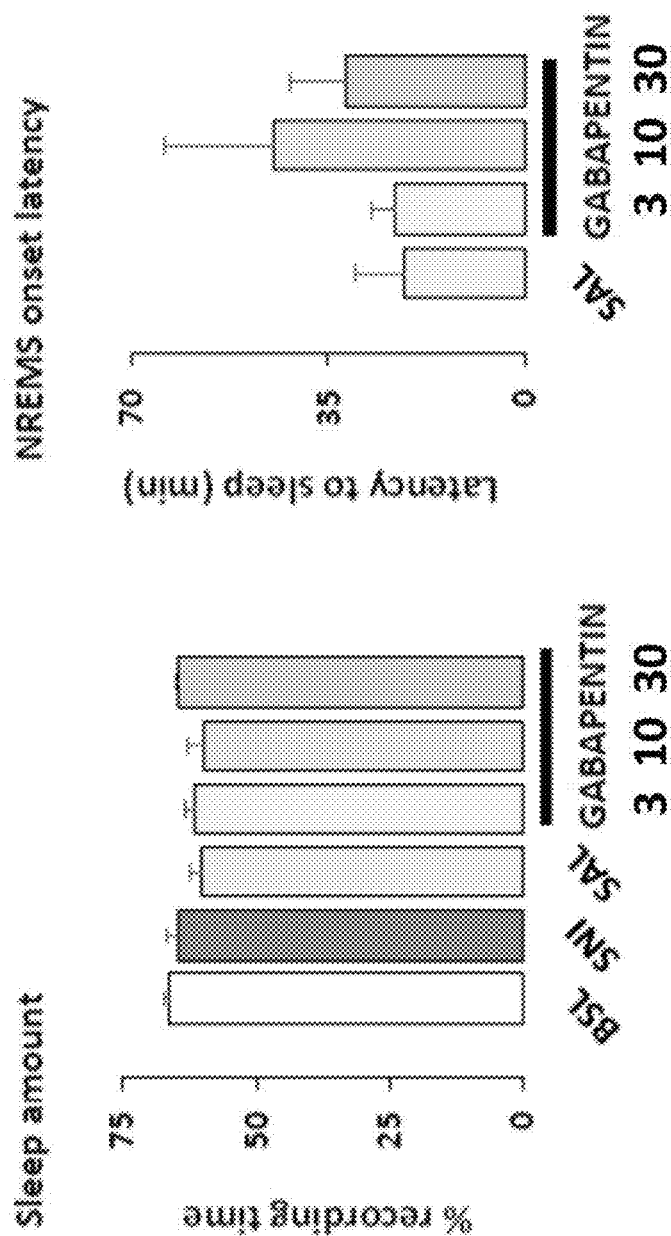
FIG. 8C. The total amount of NREMS for SNI mice with and without GBP treatment.
FIG. 8D. Latency to fall asleep (NREMS) for SNI mice with and without GBP treatment.

As shown in FIG. 8A, gabapentin (GBP) restored the average length of NREMS in SNI mice. At 30 mg/kg, the length of average NREMS was similar to the average length of NREMS before the surgery. These effects were the strongest within 0-2 hours after the administration (FIG. 8B). However, the total amount of sleep were not affected the GBP. And there was slight increase of latency on sleep (FIG. 8D), which is the length of time that it takes to accomplish the transition from full wakefulness to sleep. Thus, the results showed that GBP restored normal sleep without causing sedation in SNI mice.

FIGS. 8E-8G show the mean duration, bout number, and percentage of wake, NREM, and REM. The results similarly indicated that the carbamazepine restored the average length of NREM, and it did not induce sedation.

Peripheral nerve injury caused by trauma has high prevalence of spontaneous paroxysmal pain in patients. The results show that the anticonvulsant drugs (e.g. anti-epileptic compounds) are effective against this type of pain. These compounds can restore normal sleep in SNI mice at doses that do not cause sedation and are close to plasma level of patients with pain relief.

Example 8

Mice Developed Pain Hypersensitivity, but Their Sleep was Unaffected After Skin Incision Pain hypersensitivity alone is not sufficient to cause major sleep disturbances. Total sleep amount was not affected by SNI or Sciatic Nerve Crush. To confirm this, experiments were performed to test mice after skin incision, a procedure that causes mechanical allodynia of similar amplitude to that after SNI.

Statistical analysis was performed using Prism version 7.00 for Windows, GraphPad Software (La Jolla, CA, USA). Quantitative data are presented as mean±SEM. All experiments were independently repeated at least twice. Normality was assessed using the Shapiro-Wilk test. A Student's t-test was used to determine significance between two groups, and F-tests for equality of variance were used for all t-tests to compare variances. Comparison between more than two groups were analyzed by one- or two-way ANOVA with repeated measures when appropriate. Bartlett's test was used to test variance for all one-way ANOVA. For experiments that included sham animals, between-subject analyses were performed to compare sham to SNI or SNC mice. Where appropriate, within-subject analyses were performed to compare baseline and nerve injury surgery (in this case, animals served as their own control). In the case of significance, ANOVA analysis was followed by the appropriate multiple-comparisons tests. $P \leq 0.05$ was considered significant. The effect size for each data set was calculated: (partial) $\eta 2$ or $\eta 2p$ for factorial analyses (ANOVA) and Cohen's d for t-tests. Sample size was determined on the basis of previous studies carried out in the laboratory.

Figures 9A, 9B:
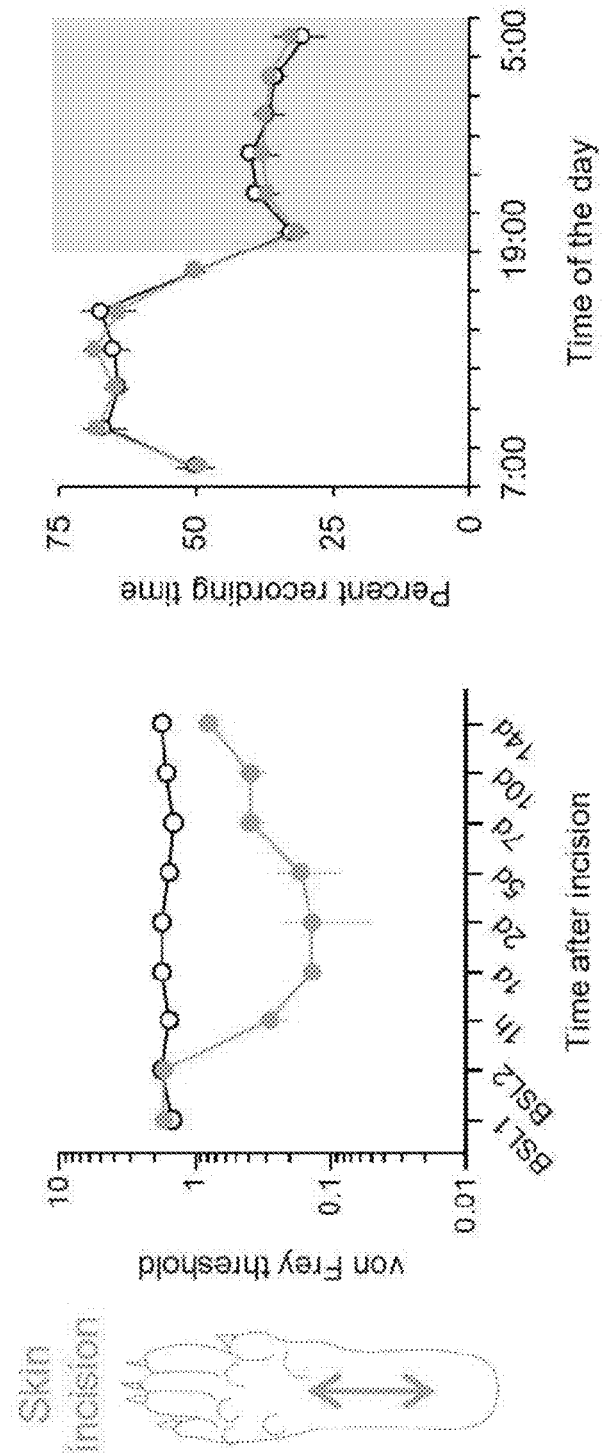
FIG. 9A. Mice developed mechanical pain hypersensitivity after skin incision.
FIG. 9B. NREMS was not affected after skin incision in mice.

The results showed that the sleep-wake patterns were not altered by pain hypersensitivity alone, and the number of brief awakenings was not increased as compared to baseline (FIGS. 9A-9B).

Example 9

Sleep Fragmentation is Specific to NREMS

Figure 10A:
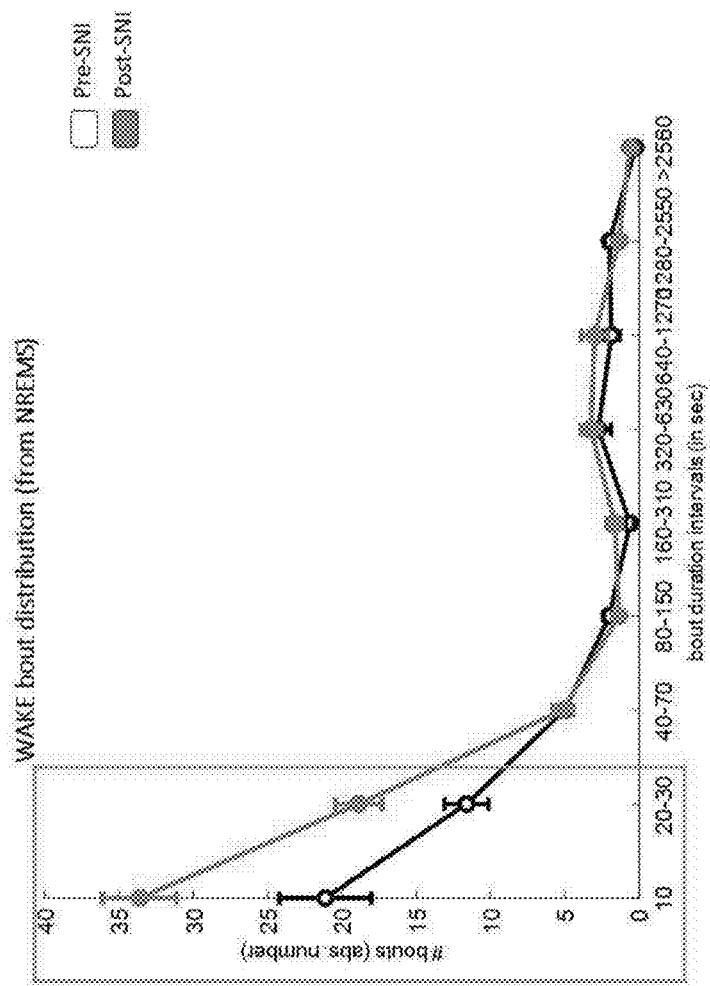
FIG. 10A. Distribution of the length of wake bouts during NREMS in mice before and after SNI.
Figure 10B:
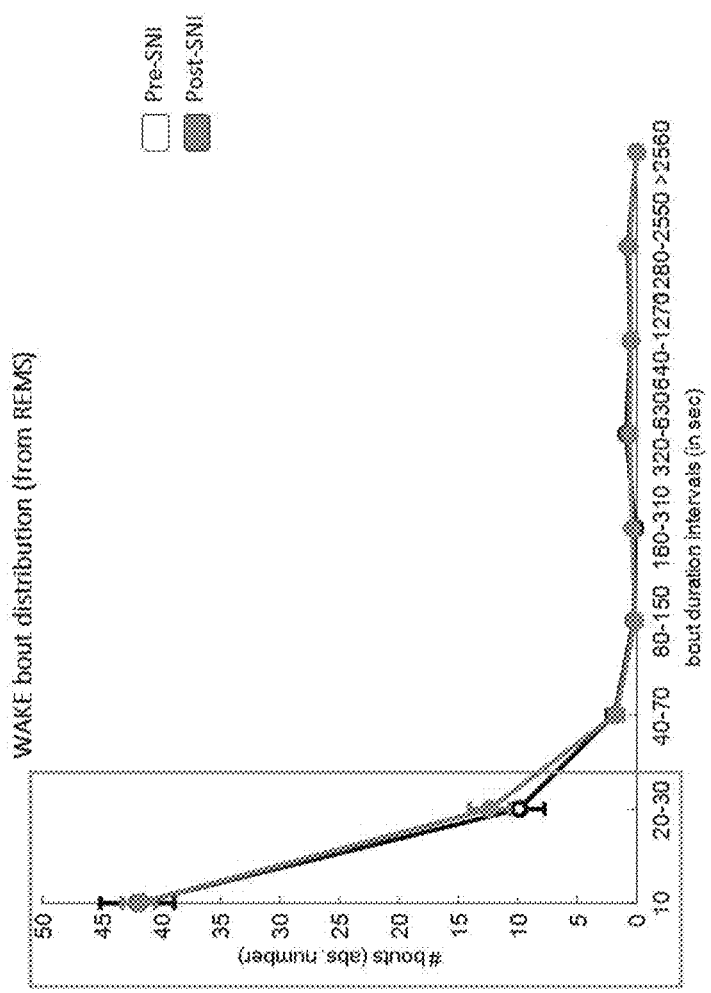
FIG. 10B. Distribution of the length of wake bouts during REMS in mice before and after SNI.
Figure 11:
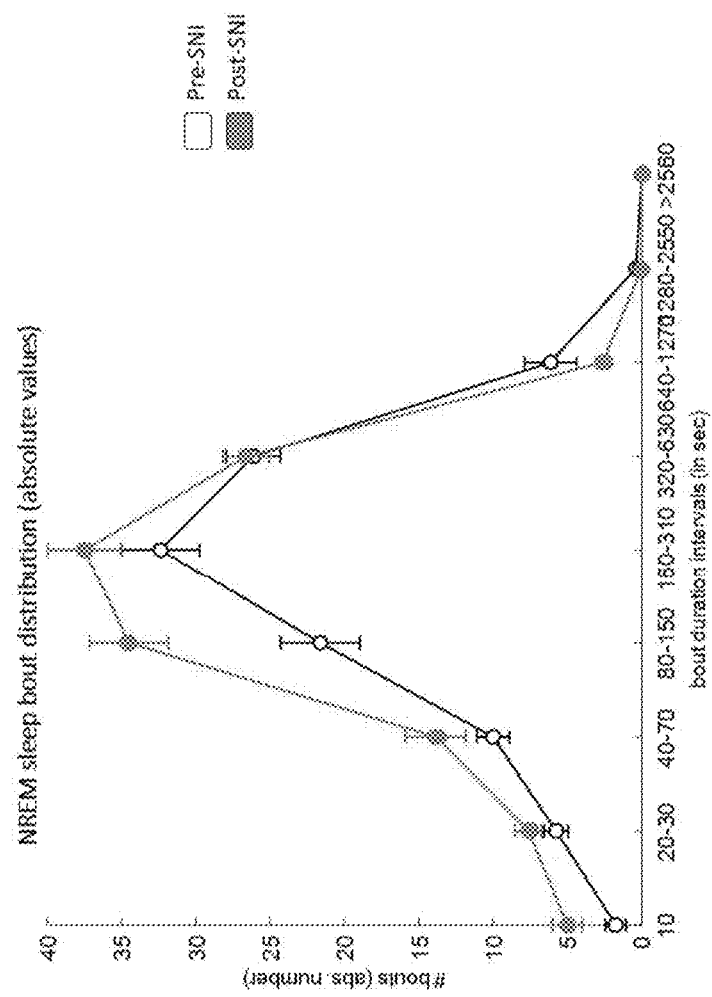
FIG. 11. Distribution of the length of NREMS episodes in mice before and after SNI.

Experiments were performed to determine the length of wake bouts during NREMS and REMS in pre-SNI mice and post-SNI mice. As shown in FIG. 10A, post-SNI mice had significantly more short awakenings (e.g., lasting from 10 to 30 seconds) during NREMS as compared to pre-SNI mice. However, neuropathic pain did not affect wake bouts that are longer than 40 seconds. In FIG. 10B, there were no difference for wake bouts following REM sleep episodes between pre-SNI mice and post-SNI mice. Thus, Sleep fragmentation is specific to NREMS, and brief awakenings during NREMS (or that disrupt NREMS) can be used as a biomarker for neuropathic pain. FIG. 11 further shows that mice with neuropathic pain (post-SNI) had fewer long episodes of NREMS.

Example 10

Chronic Inflammation Does Not Cause Sleep Fragmentation

Figure 12A:
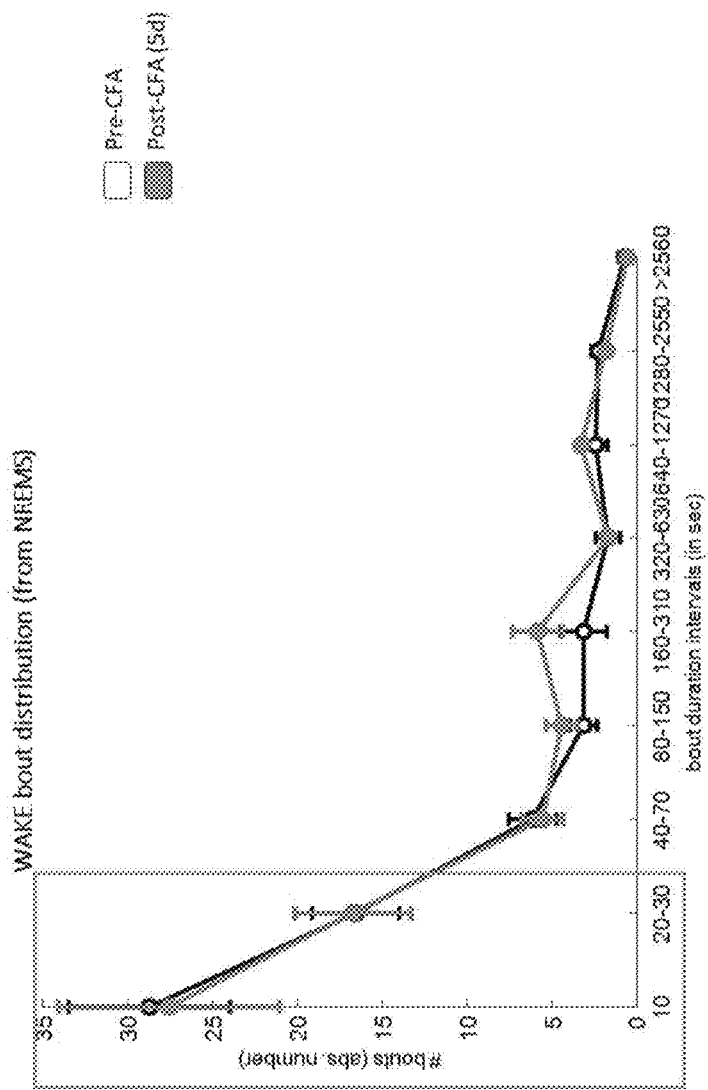
FIG. 12A. Distribution of the length of wake bouts during NREMS in mice without chronic inflammation (pre-CFA) and mice with chronic inflammation (post-CFA).
Figure 12B:
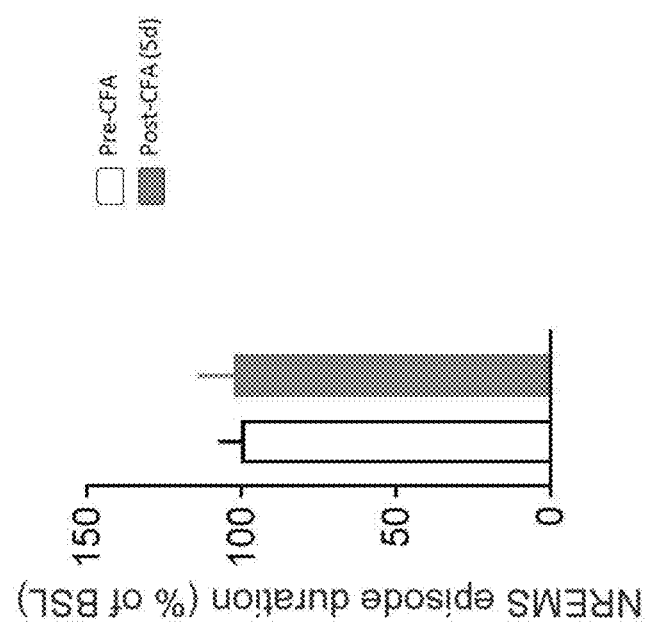
FIG. 12B. The average length of NREMS episodes in mice without chronic inflammation (pre-CFA) and mice with chronic inflammation (post-CFA) expressed in percent of their baseline.

Experiments were performed to determine whether chronic inflammation can cause sleep fragmentation. Mice were treated with Complete Freund's Adjuvant (CFA at 1 mg/ml; 20 ul injected intraplantarly once) to induce chronic inflammation. The length of wake bouts in mice with chronic inflammation (post-CFA) and without chronic inflammation (pre-CFA) were determined. As shown in FIG. 12A, there were no differences between mice with chronic inflammation (post-CFA) and without chronic inflammation (pre-CFA). The result indicates that chronic inflammation and pain (if any) caused by chronic inflammation cannot cause sleep fragmentation. FIG. 12B further shows that there was no significant difference in terms of the average length of NREMS in mice with chronic inflammation (post-CFA) and without chronic inflammation (pre-CFA). This result indicates that non-neuropathic pain (e.g., inflammatory pain) do not cause sleep fragmentation.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject having neuropathic pain, the method comprising:
   detecting the frequency of brief awakenings (BAs) during sleep of the subject, wherein the BAs last less than 30s;
   determining that the frequency of BAs is increased compared to a reference level; and
   administering a therapeutic agent to the subject, thereby treating neuropathic pain in the subject.

2. The method of claim 1, wherein the neuropathic pain is spontaneous neuropathic pain.

3. The method of claim 1, wherein the therapeutic agent is an analgesic agent.

4. The method of claim 3, wherein the analgesic agent is a narcotic analgesic, an anticonvulsant agent, a corticosteroid, a secondary amine tricyclic antidepressant (TCA), a selective serotonin norephinephrine reuptake inhibitor, a calcium channel a2-d ligand, a N-methyl-D-aspartate (NMDA) receptor antagonist, or a sepiapterin reductase inhibitor, or any combination thereof.

5. The method of claim 3, wherein the analgesic agent is alfentanil, almotriptan, buprenorphine, butalbital, butorphanol, codeine, diflunisal, dihydrocodeine, diphenhydramine, eletriptan, ergotamine, fentanyl, frovatriptan, gabapentanoid, hydrocodone, hydromorphone, isometheptene mucate, levorphanol, mefenamic acid, meperidine, methadone, morphine, nalbuphine, naratriptan, oxycodone, oxymorphone, phenyltoloxamine, piroxicam, propoxyphene, rizatriptan, sumatriptan, tapentadol, tolmetin, tramadol, ziconotide, zolmitriptan, nortriptyline, desipramine, duloxetine, venlafaxine, gabapentin, pregabalin, lidocaine, Carbamazepine, Lacosamide, Lamotrigine, Oxcarbazepine, Topiramate, Valproate, sulfasalazine, capsaicin, Mexiletine, dextromethorphan, memantine, Tetrahydrocannabinol, or botulin toxin, or any combination thereof.

6. The method of claim 1, wherein the BAs disrupt non-rapid eye movement sleep (NREMS) of the subject.

7. The method of claim 1, wherein the reference level is the average frequency of BAs in subjects who do not have neuropathic pain.

8. The method of claim 1, wherein the frequency of BAs of the subject is at least 20% more than the reference level.

9. The method of claim 1, wherein the frequency of BAs is measured by the number of BAs during sleep.

10. The method of claim 1, wherein each BA lasts from 2 seconds to 30 seconds.

11. The method of claim 1, wherein the BAs are detected by electroencephalogram (EEG) and electromyogram (EMG).

12. The method of claim 11, wherein the BAs are characterized by a high-frequency low amplitude EEG signal and an increase of EMG tone.

13. The method of claim 1, wherein the subject is a human subject.

* * * * *